(12) United States Patent
Beasley et al.

(10) Patent No.: US 6,936,453 B2
(45) Date of Patent: *Aug. 30, 2005

(54) ISOLATED HUMAN PHOSPHOLIPASE PROTEINS, NUCLEIC ACID MOLECULES ENCODING HUMAN PHOSPHOLIPASE PROTEINS, AND USES THEREOF

(75) Inventors: Ellen M Beasley, Darnestown, MD (US); Chunhua Yan, Boyds, MD (US); Valentina Di Francesco, Rockville, MD (US)

(73) Assignee: Applera Corporation, Norwalk, CT (US)

( * ) Notice: Subject to any disclaimer, the term of this patent is extended or adjusted under 35 U.S.C. 154(b) by 47 days.

This patent is subject to a terminal disclaimer.

(21) Appl. No.: 10/636,579

(22) Filed: Aug. 8, 2003

(65) Prior Publication Data

US 2004/0029246 A1 Feb. 12, 2004

Related U.S. Application Data

(62) Division of application No. 10/020,121, filed on Dec. 18, 2001, now Pat. No. 6,638,747, which is a division of application No. 09/801,052, filed on Mar. 8, 2001, now Pat. No. 6,368,842.

(60) Provisional application No. 60/255,386, filed on Dec. 15, 2000.

(51) Int. Cl.[7] .................... C12N 9/20; C12N 1/20; C12N 15/00; C12P 21/04; C07H 21/04

(52) U.S. Cl. .................... 435/198; 435/4; 435/6; 435/252.3; 435/320.1; 435/69.7; 435/71.1; 435/440; 536/23.2; 536/23.5

(58) Field of Search .................... 435/198, 4, 6, 435/69.1, 71.1, 252.3, 320.1, 440; 536/23.2, 23.5

(56) References Cited

U.S. PATENT DOCUMENTS 6,368,842 B1 * 4/2002 Beasley et al. ............. 435/198

* cited by examiner

Primary Examiner—Manjunath Rao
Assistant Examiner—Yong Pak
(74) Attorney, Agent, or Firm—Celera Genomics; Lin Sun-Hoffman

(57) ABSTRACT

The present invention provides amino acid sequences of peptides that are encoded by genes within the human genome, the phospholipase peptides of the present invention. The present invention specifically provides isolated peptide and nucleic acid molecules, methods of identifying orthologs and paralogs of the phospholipase peptides, and methods of identifying modulators of the phospholipase peptides.

11 Claims, 18 Drawing Sheets

```
   1 GACCCTGACA CACCCACCTT CTCACCTGGG CTCTGCGTAT CCCCCAGCCT
  51 TGAGGGAAGA TGAAGCCTAA ACTGATGTAC CAGGAGAAAG CCCGCTGGGT
 101 CCTGCTGGTC CTCATTCTGG CGGTTGTGGG CTTCGGAGCC CTGATGACTC
 151 AGCTGTTTCT ATGGGAATAC GGCGACTTGC ATCTCTTTGG GCCCAACCAG
 201 CGCCCAGCCC CCTGCTATGA CCCTTGCGAA GCAGTGCTGG TGGAAAGCAT
 251 TCCTGAGGGC CTGGACTTCC CCAATGCCTC CACGGGGAAC CCTTCCACCA
 301 GCCAGGCCTG GCTGGGCCTG CTCGCCGGTG CGCACAGCAG CCTGGACATC
 351 GCCTCCTTCT ACTGGACCCT CACCAACAAT GACACCCACA CGCAGGAGCC
 401 CTCTGCCCAG CAGGGTGAGG AGGTCCTCCG GCAAGCTGCAG ACCCTGGCAC
 451 CAAAGGGCGT GAACGTCCGC ATCGCTGTGA GCAAGCCCAG CGGGCCCCAG
 501 CCACAGGCGG ACCTGCAGGC TCTGCTGCAG AGCGGTGCCC AGGTCCGCAT
 551 GGTGGACATG CAGAAGCTGA CCCATGGCGT CCTGCATACC AAGTTCTGGG
 601 TGGTGGACCA GACCCACTTC TACCTGGGCA GTGCCAACAT GGACTGGCGT
 651 TCACTGACCC AGGTCAAGGA GCTGGGCGTG GTCATGTACA ACTGCAGCTG
 701 CCTGGCTCGA GACCTGACCA AGATCTTTGA GGCTACTGG TTCCTGGGCC
 751 AGGCAGGCAG CTCCATCCCA TCAACTTGGC CCCGGTTCTA TGACACCCGC
 801 TACAACCAAG AGACACCAAT GGAGATCTGC CTCAATGGAA CCCCTGCTCT
 851 GGCCTACCTG GCGAGTGCGC CCCCACCCCT GTGTCCAAGT GGCCGCACTC
 901 CAGACCTGAA GGCTCTACTC AACGTGGTGG ACAATGCCCG GAGTTTCATC
 951 TACGTCGCTG TCATGAACTA CCTGCCCACT CTGGAGTTCT CCCACCCTCA
1001 CAGGTTCTGG CCTGCCATTG ACGATGGGCT GCGGCGGGCC ACCTACGAGC
1051 GTGGCGTCAA GGTGCGCCTG CTCATCAGCT GCTGGGGACA CTCGGAGCCA
1101 TCCATGCGGG CCTTCCTGCT CTCTCTGGCT GCCCTGCGTG ACAACCATAC
1151 CCACTCTGAC ATCCAGGTGA AACTCTTTGT GGTCCCCGCG GATGAGGCCC
1201 AGGCTCGAAT CCCATATGCC CGTGTCAACC ACAACAAGTA CATGGTGACT
1251 GAACGCGCCA CCTACATCGG AACCTCCAAC TGGTCTGGCA ACTACTTCAC
1301 GGAGACGGCG GGCACCTCGC TGCTGGTGAC GCAGAATGGG AGGGGCGGCC
1351 TGCGGAGCCA GCTGGAGGCC ATTTCCTGA GGGACTGGGA CTCCCCTTAC
1401 AGCCATGACC TTGACACCTC AGCTGACAGC GTGGGCAACG CCTGCCGCCT
1451 GCTCTGAGGC CCGATCCAGT GGGCAGGCCA AGGCCTGCTG GGCCCCCGCG
1501 GACCCAGGTG CTCTGGGTCA CGGTCCCTGT CCCCGCACCC CCGCTTCTGT
1551 CTGCCCCATT GTGGCTCCTC AGGCTCTCTC CCCTGCTCTC CCACCTCTAC
1601 CTCCACCCCC ACCGGGCCTG ACGCTGTGGC CCCGGGACCC AGCAGAGCTG
1651 GGGGAGGGAT CAGCCCCCAA AGAAATGGGG GTGCATGCTG GGCCTGGCCC
1701 CCTGGCCCAC CCCCACTTTC CAGGGCAAAA AGGGCCCAGG GTTATAATAA
1751 GTAAATAACT TGTCTGTAAA AAAAAAAAA AAAAAAAAA AAAAAAAAAA
1801 AAAAAAAAAA AAAAAAAAAA AAAAAAAAAA AAAAAAAAAA AAAAAAAAAA
1851 AAAAAAAAAA AAAAAAAAA AA (SEQ ID NO:1)

FEATURES:
5'UTR:        1 - 59
Start Codon:  60
Stop Codon:   1455
3'UTR:        1458
```

```
   1 GACCCTGACA CACCCACCTT CTCACCTGGG CTCTGCGTAT CCCCCAGCCT
  51 TGAGGGAAGA TGAAGCCTAA ACTGATGTAC CAGGAGAAAG CCCGCTGGGT
 101 CCTGCTGGTC CTCATTCTGG CGGTTGTGGG CTTCGGAGCC CTGATGACTC
 151 AGCTGTTTCT ATGGGAATAC GGCGACTTGC ATCTCTTTGG GCCCAACCAG
 201 CGCCCAGCCC CCTGCTATGA CCCTTGCGAA GCAGTGCTGG TGGAAAGCAT
 251 TCCTGAGGGC CTGGACTTCC CCAATGCCTC CACGGGGAAC CCTTCCACCA
 301 GCCAGGCCTG GCTGGGCCTG CTCGCCGGTG CGCACAGCAG CCTGGACATC
 351 GCCTCCTTCT ACTGGACCCT CACCAACAAT GACACCCACA CGCAGGAGCC
 401 CTCTGCCCAG CAGGGTGAGG AGGTCCTCCG GCAGCTGCAG ACCCTGGCAC
 451 CAAAGGGCGT GAACGTCCGC ATCGCTGTGA GCAAGCCCAG CGGGCCCCAG
 501 CCACAGGCGG ACCTGCAGGC TCTGCTGCAG AGCGGTGCCC AGGTCCGCAT
 551 GGTGGACATG CAGAAGCTGA CCCATGGCGT CCTGCATACC AAGTTCTGGG
 601 TGGTGGACCA GACCCACTTC TACCTGGGCA GTGCCAACAT GGACTGGCGT
 651 TCACTGACCC AGGTCAAGGA GCTGGGCGTG GTCATGTACA ACTGCAGCTG
 701 CCTGGCTCGA GACCTGACCA AGATCTTTGA GGCCTACTGG TTCCTGGGCC
 751 AGGCAGGCAG CTCCATCCCA TCAACTTGGC CCCGGTTCTA TGACACCCGC
 801 TACAACCAAG AGACACCAAT GGAGATCTGC CTCAATGGAA CCCCTGCTCT
 851 GGCCTACCTG GCGAGTGCGC CCCCACCCCT GTGTCCAAGT GGCCGCACTC
 901 CAGACCTGAA GGCTCTACTC AACGTGGTGG ACAATGCCCG GAGTTTCATC
 951 TACGTCGCTG TCATGAACTA CCTGCCCACT CTGGAGTTCT CCCACCCTCA
1001 CAGGTTCTGG CCTGCCATTG ACGATGGGCT GCGGCGGGCC ACCTACGAGC
1051 GTGGCGTCAA GGTGCGCCTG CTCATCAGCT GCTGGGGACA CTCGGAGCCA
1101 TCCATGCGGG CCTTCCTGCT CTCTCTGGCT GCCCTGCGTG ACAACCATAC
1151 CCACTCTGAC ATCCAGGTGA AACTCTTTGT GGTCCCCGCG GATGAGGCCC
1201 AGGCTCGAAT CCCATATGCC CGTGTCAACC ACAACAAGTA CATGGTGACT
1251 GAACGCGCCA CCTACATCGG AACCTCCAAC TGGTCTGGCA ACTACTTCAC
1301 GGAGACGGCG GGCACCTCGC TGCTGGTGAC GCAGAATGGG AGGGGCGGCC
1351 TGCGGAGCCA GCTGGAGGCC ATTTTCCTGA GGGACTGGGA CTCCCCTTAC
1401 AGCCATGACC TTGACACCTC AGCTGACAGC GTGGGCAACG CCTGCCGCCT
1451 GCTCTGAGGC CCGATCCAGT GGGCAGGCCA AGGCCTGCTG GGCCCCCGCG
1501 GACCCAGGTG CTCTGGGTCA CGGTCCCTGT CCCCGCACCC CCGCTTCTGT
1551 CTGCCCCATT GTGGCTCCTC AGGCTCTCTC CCCTGCTCTC CCACCTCTAC
1601 CTCCACCCCC ACCGGGCCTG ACGCTGTGGC CCCGGGACCC AGCAGAGCTG
1651 GGGGAGGGAT CAGCCCCCAA AGAAATGGGG GTGCATGCTG GGCCTGGCCC
1701 CCTGGCCCAC CCCCACTTTC CAGGGCAAAA AGGGCCCAGG GTTATAATAA
1751 GTAAATAACT TGTCTGTAAA AAAAAAAAAA AAAAAAAAAA AAAAAAAAAA
1801 AAAAAAAAAA AAAAAAAAAA AAAAAAAAAA AAAAAAAAAA AAAAAAAAAA
1851 AAAAAAAAAA AAAAAAAAAA AA  (SEQ ID NO:1)
```

FEATURES:
5'UTR:        1 - 59
Start Codon:  60
Stop Codon:   1455
3'UTR:        1458

FIGURE 1A

Homologous proteins:
Top 10 BLAST Hits

```
                                                                Score    E
gi|7110641|ref|NP_036400.1| similar to vaccinia virus HindIII K...  912   0.0
gi|7242181|ref|NP_035246.1| phospholipase D3 [Mus musculus] >gi...  898   0.0
gi|7298757|gb|AAF53968.1| (AE003669) CG9248 gene product [alt 1...  377   e-103
gi|9790946|ref|NP_063673.1| K4L; putative [Vaccinia virus] >gi|...  369   e-101
gi|138615|sp|P18377|VK04_VACCV PROTEIN K4 (PROTEIN K3) >gi|7427...  368   e-100
gi|7460907|pir||T30777 hypothetical protein 25L - vaccinia viru...  367   e-100
gi|1808630|emb|CAA64112.1| (X94355) M4L [Cowpox virus] >gi|2285...  366   e-100
gi|7498773|pir||T32489 hypothetical protein F09G2.8 - Caenorhab...  316   5e-85
gi|832928|gb|AAA67429.1| (M19469) ORF [Dictyostelium discoideum]    252   9e-66
gi|10728907|gb|AAF53972.2| (AE003669) CG9243 gene product [Dros...  248   2e-64
```

BLAST to dbEST:

```
                                            Score    E
gi|1270757  /dataset=dbest  /taxon=9606 ...  2131   0.0
gi|9806165  /dataset=dbest  /taxon=960...    1441   0.0
gi|11264276 /dataset=dbest  /taxon=96...     1382   0.0
gi|11100168 /dataset=dbest  /taxon=960...    1358   0.0
gi|11262891 /dataset=dbest  /taxon=96...     1334   0.0
gi|10327478 /dataset=dbest  /taxon=96...     1277   0.0
gi|9189018  /dataset=dbest  /taxon=960...    1269   0.0
gi|10157120 /dataset=dbest  /taxon=96...     1259   0.0
gi|9189336  /dataset=dbest  /taxon=960...    1225   0.0
```

EXPRESSION INFORMATION FOR MODULATORY USE:
library source:
Expression information from BLAST dbEST hits:
gi|1270757  Human Infant brain
gi|9806165  Human uterus
gi|11264276 Human brain nuroblastoma
gi|11100168 Human brain nuroblastoma
gi|11262891 Human brain nuroblastoma
gi|10327478 Human lung
gi|9189018  Human Ovary adenocarcinoma
gi|10157120 Human Ovary adenocarcinoma
gi|9189336  Human Ovary adenocarcinoma Expression information from PCR-based tissue screening panels:
Human leukocytes

FIGURE 1B

```
  1 MKPKLMYQEK ARWVLLVLIL AVVGFGALMT QLFLWEYGDL HLFGPNQRPA
 51 PCYDPCEAVL VESIPEGLDF PNASTGNPST SQAWLGLLAG AHSSLDIASF
101 YWTLTNNDTH TQEPSAQQGE EVLRQLQTLA PKGVNVRIAV SKPSGPQPQA
151 DLQALLQSGA QVRMVDMQKL THGVLHTKFW WDQTHFYLG SANMDWRSLT
201 QVKELGVVMY NCSCLARDLT KIFEAYWFLG QAGSSIPSTW PRFYDTRYNQ
251 ETPMEICLNG TPALAYLASA PPPLCPSGRT PDLKALLNVV DNARSFIYVA
301 VMNYLPTLEF SHPHRFWPAI DDGLRRATYE RGVKVRLLIS CWGHSEPSMR
351 AFLLSLAALR DNHTHSDIQV KLFVVPADEA QARIPYARVN HNKYMVTERA
401 TYIGTSNWSG NYFTETAGTS LLVTQNGRGG LRSQLEAIFL RDWDSPYSHD
451 LDTSADSVGN ACRLL  (SEQ ID NO:2)
```

FEATURES:
Functional domains and key regions:
[1] PDOC00001 PS00001 ASN_GLYCOSYLATION
N-glycosylation site Number of matches: 5
    1    72-75 NAST
    2   107-110 NDTH
    3   211-214 NCSC
    4   362-365 NHTH
    5   407-410 NWSG

[2] PDOC00004 PS00004 CAMP_PHOSPHO_SITE
cAMP- and cGMP-dependent protein kinase phosphorylation site 325-328 RRAT

[3] PDOC00005 PS00005 PKC_PHOSPHO_SITE
Protein kinase C phosphorylation site

Number of matches: 3
    1   277-279 SGR
    2   348-350 SMR
    3   397-399 TER

[4] PDOC00006 PS00006 CK2_PHOSPHO_SITE
Casein kinase II phosphorylation site

Number of matches: 7
    1    63-66 SIPE
    2    93-96 SSLD
    3   105-108 TNND
    4   252-255 TPME
    5   364-367 THSD

FIGURE 2A

```
     6    433-436  SQLE
     7    453-456  TSAD
```

[5] PDOC00007 PS00007 TYR_PHOSPHO_SITE
Tyrosine kinase phosphorylation site

Number of matches: 2
```
     1    242-248  RFYDTRY
     2    441-447  RDWDSPY
```

[6] PDOC00008 PS00008 MYRISTYL
N-myristoylation site

Number of matches: 9
```
     1     26-31   GALMTQ
     2     76-81   GNPSTS
     3     86-91   GLLAGA
     4     90-95   GAHSSL
     5    173-178  GVLHTK
     6    230-235  GQAGSS
     7    323-328  GLRRAT
     8    410-415  GNYFTE
     9    429-434  GGLRSQ
```

[7] PDOC00266 PS00294 PRENYLATION
Prenyl group binding site (CAAX box)

462-465 CRLL

<u>Membrane spanning structure and domains:</u>
```
  Helix  Begin   End   Score  Certainty
    1     19     39    2.209  Certain
    2     89     109   0.787  Putative
    3    227     247   0.682  Putative
    4    264     284   0.996  Putative
```

FIGURE 2B

```
BLAST Alignment to Top Hit:
>gi|7110641|ref|NP_036400.1| similar to vaccinia virus HindIII K4L ORF
            [Homo sapiens]
  gb|AAB16799.1| (U60644) HU-K4 [Homo sapiens]
            Length = 437

Score =  912 bits (2330), Expect = 0.0
  Identities = 436/437 (99%), Positives = 436/437 (99%)
  Frame = +3

Query: 144   MTQLFLWEYGDLHLFGPNQRPAPCYDPCEAVLVESIPEGLDFPNASTGNPSTSQAWLGLL 323
             MTQLFLWEYGDLHLFGPNQRPAPCYDPCEAVLVESIPEGLDFPNASTGNPSTSQAWLGLL
Sbjct: 1     MTQLFLWEYGDLHLFGPNQRPAPCYDPCEAVLVESIPEGLDFPNASTGNPSTSQAWLGLL 60

Query: 324   AGAHSSLDIASFYWTLTNNDTHTQEPSAQQGEEVLRQLQTLAPKGVNVRIAVSKPSGPQP 503
             AGAHSSLDIASFYWTLTNNDTHTQEPSAQQGEEVLRQLQTLAPKGVNVRIAVSKPSGPQP
Sbjct: 61    AGAHSSLDIASFYWTLTNNDTHTQEPSAQQGEEVLRQLQTLAPKGVNVRIAVSKPSGPQP 120

Query: 504   QADLQALLQSGAQVRMVDMQKLTHGVLHTKFWVVDQTHFYLGSANMDWRSLTQVKELGVV 683
             QADLQALLQSGAQVRMVDMQKLTHGVLHTKFWVVDQTHFYLGSANMDWRSLTQVKELGVV
Sbjct: 121   QADLQALLQSGAQVRMVDMQKLTHGVLHTKFWVVDQTHFYLGSANMDWRSLTQVKELGVV 180

Query: 684   MYNCSCLARDLTKIFEAYWFLGQAGSSIPSTWPRFYDTRYNQETPMEICLNGTPALAYLA 863
             MYNCSCLARDLTKIFEAYWFLGQAGSSIPSTWPRFYDTRYNQETPMEICLNGTPALAYLA
Sbjct: 181   MYNCSCLARDLTKIFEAYWFLGQAGSSIPSTWPRFYDTRYNQETPMEICLNGTPALAYLA 240

Query: 864   SAPPPLCPSGRTPDLKALLNVVDNARSFIYVAVMNYLPTLEFSHPHRFWPAIDDGLRRAT 1043
             SAPPPLCPSGRTPDLKALLNVVDNARSFIYVAVMNYLPTLEFSHPHRFWPAIDDGLRRAT
Sbjct: 241   SAPPPLCPSGRTPDLKALLNVVDNARSFIYVAVMNYLPTLEFSHPHRFWPAIDDGLRRAT 300

Query: 1044  YERGVKVRLLISCWGHSEPSMRAFLLSLAALRDNHTHSDIQVKLFVVPADEAQARIPYAR 1223
             YERGVKVRLLISCWGHSEPSMRAFLLSLAALRDNHTHSDIQVKLFVVPADEAQARIPYAR
Sbjct: 301   YERGVKVRLLISCWGHSEPSMRAFLLSLAALRDNHTHSDIQVKLFVVPADEAQARIPYAR 360

Query: 1224  VNHNKYMVTERATYIGTSNWSGNYFTETAGTSLLVTQNGRGGLRSQLEAIFLRDWDSPYS 1403
             VNHNKYMVTERATYIGTSNWSGNYFTETAGTSLLVTQNGRGGLRSQLEAIFLRDWDSPY
Sbjct: 361   VNHNKYMVTERATYIGTSNWSGNYFTETAGTSLLVTQNGRGGLRSQLEAIFLRDWDSPYI 420

Query: 1404  HDLDTSADSVGNACRLL 1454
             HDLDTSADSVGNACRLL
Sbjct: 421   HDLDTSADSVGNACRLL 437   (SEQ ID NO:4)
```

FIGURE 2C

>gi|7242181|ref|NP_035246.1| phospholipase D3 [Mus musculus]
 gb|AAC73069.1| (AF026124) schwannoma-associated protein [Mus musculus]
     Length = 488

Score = 898 bits (2295), Expect = 0.0
Identities = 435/490 (88%), Positives = 453/490 (91%), Gaps = 25/490 (5%)
Frame = +3

```
Query:   60  MKPKLMYQE----------------------KARWVLLVLILAVVGFGALMTQLFLW 164
             MKPKLMYQE                      KARWVLLVLILAVVGFGALMTQLFLW
Sbjct:    1  MKPKLMYQELKVPVEEPAGELPLNEIEAWKAAEKKARWVLLVLILAVVGFGALMTQLFLW  60

Query:  165  EYGDLHLFGPNQRPAPCYDPCEAVLVESIPEGLDFPNASTGNPSTSQAWLGLLAGAHSSL 344
             EYGDLHLFGPNQRPAPCYDPCEAVLVESIPEGL+FPNA+T NPSTSQAWLGLLAGAHSSL
Sbjct:   61  EYGDLHLFGPNQRPAPCYDPCEAVLVESIPEGLEFPNATTSNPSTSQAWLGLLAGAHSSL 120

Query:  345  DIASFYWTLTNNDTHTQEPSAQQGEEVLRQLQTLAPKGVNVRIAVSKPSGPQPQADLQAL 524
             DIASFYWTLTNNDTHTQEPSAQQGEEVL+QLQ LAP+GV VRIAVSKP+GP   ADLQ+L
Sbjct:  121  DIASFYWTLTNNDTHTQEPSAQQGEEVLQQLQALAPRGVKVRIAVSKPNGPL--ADLQSL 178

Query:  525  LQSGAQVRMVDMQKLTHGVLHTKFWVVDQTHFYLGSANMDWRSLTQVKELGVVMYNCSCL 704
             LQSGAQVRMVDMQKLTHGVLHTKFWVVDQTHFYLGSANMDWRSLTQVKELGVVMYNCSCL
Sbjct:  179  LQSGAQVRMVDMQKLTHGVLHTKFWVVDQTHFYLGSANMDWRSLTQVKELGVVMYNCSCL 238

Query:  705  ARDLTKIFEAYWFLGQAGSSIPSTWPRFYDTRYNQETPMEICLNGTPALAYLASAPPPLC 884
             ARDLTKIFEAYWFLGQAGSSIPSTWPR +DTRYNQETPMEICLNGTPALAYLASAPPPLC
Sbjct:  239  ARDLTKIFEAYWFLGQAGSSIPSTWPRSFDTRYNQETPMEICLNGTPALAYLASAPPPLC 298

Query:  885  PSGRTPDLKALLNVVDNARSFIYVAVMNYLPTLEFSHPHRFWPAIDDGLRRATYERGVKV 1064
             PSGRTPDLKALLNVVD+ARSFIY+AVMNYLPT+EFSHP RFWPAIDDGLRRA YERGVKV
Sbjct:  299  PSGRTPDLKALLNVVDSARSFIYIAVMNYLPTMEFSHPRRFWPAIDDGLRRAAYERGVKV 358

Query: 1065  RLLISCWGHSEPSMRAFLLSLAALRDNHTHSDIQVKLFVVPADEAQARIPYARVNHNKYM 1244
             RLLISCWGHS+PSMR+FLLSLAAL DNHTHSDIQVKLFVVP DE+QARIPYARVNHNKYM
Sbjct:  359  RLLISCWGHSDPSMRSFLLSLAALHDNHTHSDIQVKLFVVPTDESQARIPYARVNHNKYM 418

Query: 1245  VTERATYIGTSNWSGNYFTETAGTSLLVTQNGRGGLRSQLEAIFLRDWDSPYSHDLDTSA 1424
             VTERA+YIGTSNWSG+YFTETAGTSLLVTQNG GGLRSQLEA+FLRDW+SPYSHDLDTSA
Sbjct:  419  VTERASYIGTSNWSGSYFTETAGTSLLVTQNGHGGLRSQLEAVFLRDWESPYSHDLDTSA 478

Query: 1425  DSVGNACRLL 1454
             +SVGNACRLL
Sbjct:  479  NSVGNACRLL 488   (SEQ ID NO:5)
```

FIGURE 2D

Hmmer search results (Pfam):

| Model | Description | Score | E-value | N |
|---|---|---|---|---|
| PF00614 | Phospholipase D. Active site motif | 56.7 | 5.1e-14 | 2 |
| PF00998 | Hepatitis C virus RNA dependent RNA polymera | 5.4 | 0.54 | 1 |

Parsed for domains:

| Model | Domain | seq-f | seq-t | hmm-f | hmm-t | | score | E-value |
|---|---|---|---|---|---|---|---|---|
| PF00998 | 1/1 | 6 | 26 | .. 669 | 689 | .] | 5.4 | 0.54 |
| PF00614 | 1/2 | 171 | 198 | .. 1 | 29 | [] | 42.8 | 4.1e-10 |
| PF00614 | 2/2 | 386 | 412 | .. 1 | 29 | [] | 15.6 | 0.017 |

FIGURE 2E

```
   1 GGAGGATCAC TTGAGTCCAG GAGTTCAGCC TGGGCAATAA GCAAGACCCC
  51 GTCTATACAA AATTAAAAAA AAAAAAATTA GCTGCGGCTG GGCGCGGTGG
 101 CTCATGCCTG TAATCCCAGC ACTTTTGGGG GCCTAGACGG GCGGATCACG
 151 AGGTCAGGAG ATCGAGACCA TCCTGGCTAA CACGGTGAAA CCCCATCTCT
 201 ACTAAAAAAT ACAAAAAAAA AATTAGCCGG GCATGGTGGC GGGCGCCTGT
 251 AGTCCCAGCT ACTCGGGAAG CTGAGGTGGG CGAATTGCTC GAACCAGGGA
 301 GGTGGAGGTT GCAGTGAGCC GAGATGGCGC CACTGCACTC CAGCGTGGGA
 351 GAGACAGAGC GAGACTGCGT CTCCAAAAAA AAAAAAAAAA GCAGCTGGGC
 401 ATGGTGGCAC GTGCCTGTAG TCCAGCTGC TTGGGAGGCT GAGGCAGGAG
 451 GATTGCTTGA GCCTGGGAAG TTGAGGCCGC AGTGAGCTAT GATCATGCTG
 501 CTGCACTCCA GCCTAGGGAA CAGAACTCTG GCACTAAAAA AAGAAAAGAA
 551 AAGAAAAGAA AATAGGCTTA CAATAAAAAG CAATCTTGAC CTACCCCAAA
 601 ATCCCACTCC CTTGAAGACA ACCACTTCTG CCCTGTTGCT TCTCTCAGTA
 651 ATACTCCTTT TCTGCAGTTA TCTCTTGACT TCCTGCCATG TGTGTTTGGG
 701 GGAGCTTGAG GGAAGAGGGT GTCCCTGTCT CATTGAGAGA GGTGCCACCC
 751 TGCCGTGAAA AGAGGTGCCA CCCTCTGTCA ATTAGGAGAG GAGGGATGAG
 801 AGAGGAAAGG GGTCTCCAGT GTATTTCTCC AGCCGGGGCC TTAAATCCCT
 851 CTTGGGAGAT ATGGGATGGG GTGGATCGGA AAATAAATTT TTTTAAATCC
 901 CTACCAAAAT ATCAGCTGGC TTTTTTTAAA AAATCAAATA CCAAAATCTA
 951 AATAGACTCC AACAGAAAAT TCACCATCTC CTCTGACCTT TTCTTCCCAT
1001 CTCATGCTGT GAACTGTCTT CTGTTGACTT TATCGCTACC TTTCTTCATT
1051 CTGTTATTCA ACCATGATCT CTCCGTTTCA TTTTATAAGC GTTTTATTAA
1101 TTTCATTTAT GTATTTATTT TTGACTAGGT AATGCATGTC CATGGTACAC
1151 AAATTCACAA GGTTTGTAAA TGAGAAAAGA CGTGAGGTTC CTTTTGTTCT
1201 TTACCTGTGG CCTCCCTGCC CTACACGGG ACTCTAGGGT GGAATGTAGC
1251 AAAGCCCATC CACCAGCCAT GTACTACCCC CCAACCCGGC CAGGCTGGAG
1301 CGACCGTGTC TGGGGAGCCG AGCCCCGCTT CTCGCTGCGG TGAGCCCGGA
1351 CTGGGGCACG CACTGCGCAG ACTCCCCGCT GCAGTGGGCG GAGCTCCCAC
1401 AGGCCCCGCC CCCTCCTCCC ACCCTCGTTC AGCCTGTCCA GACAGAAGCT
1451 GGGGCCCAGC GGAGGTAGCA GCAGACGCCT GAGAGCGAGG CCGAGGCCCC
1501 TCAGGGGTAG GTGGGGGGAG GCTGGCTGGG GGGATGGGCA GCGGGGTGGC
1551 AGGGAGGCCC CGATGATCCC TGGCTGAGCT GTGTGGTGTG GGGGCACCTG
1601 AGGGCGGAGG AGCCACCTAG AATATACCCC CTGTCCCAGG GCTGAGAAAA
1651 GCCAGGCACA AAGACCTGGG GCTCCGCTGA CCTCATCCAG CGCTGCCTTT
1701 CTGGGGGTGT CTACAGGTTG GAGGAGGGAG AAGGGGGCTG CTAGAGGGGA
1751 GCTGCGTGGG TGCTGATGGG GGCAGGGTGG GCACTGCAGA GTGAAGAGCA
1801 GGCAGCAGAG CGTTGGATTT TGAGGGATTT CGAAATCCTG CTGACCAGTG
1851 ACCAGCTTCC TCTTTTTGGG GTGGTGGGCA GTGTGCCAGT GGCCCCCATG
1901 ATTATGAATA GCCCCAAGAC TAATCACTCT TCTGTGATGT CTGTCCCTGG
1951 AAAGCGTAGA ACACCCCACA CAGTGCCCAC TTTTGTTCTG CCAGTTTGGA
2001 GACCCTGACA CACCCACCTT CTCACCTGGG CTCTGCGTAT CCCCCAGCCT
2051 TGAGGGAAGA TGAAGCCTAA ACTGATGTAC CAGGAGGTAG GTGGATTGGG
2101 GGGCTCAGCA GGGTGGAACT GGGTACAGTG GGGGTGGGGG TTCCCAAGAG
2151 CCACCTGTCA CCCCCGTTGT TGTCCCCATC CCCAGCTGAA GGTGCCTGCA
2201 GAGGAGCCCG CCAATGAGCT GCCCATGAAT GAGATTGAGG CGTGGAAGGC
2251 TGCGGAAAAG GTAGGAGCCC TCCGCCACCC TCGCTCTGTC TCAGAGACAG
```

FIGURE 3A

```
2301 GCTGGGCTGC CCCCCTCGGG CTGGCTGACC ACCTCCTCCT CCCCACAGAA
2351 AGCCCGCTGG GTCCTGCTGG TCCTCATTCT GGCGGTTGTG GGCTTCGGAG
2401 CCCTGATGAC TCAGCTGTTT CTATGGGAAT ACGGCGACTT GCATCTCTTT
2451 GGGCCCAACC AGCGCCCAGC CCCCTGCTAT GACCCTTGCG AGTAAGTGGG
2501 GGGTGCTGCA CTTGGTGGGG GAGGGGCCTG CCAGACCAGG TACACTTAAG
2551 CACACACTAA ACAGGGCCTG CACTCAGCCC TACCCAGCGC TTGCGACAAG
2601 TGAGGAGGTT GCAGGCTCCC AAGTGCTCGC CCGCCCCCTC CTCCTCCACA
2651 CACATAGTTT CTATGGCAGC CACAGCGTCA TCTTCTGTCA GGCCTGTGAA
2701 CAGACACAGC ATCTTCCACC CACATCTGTG GACCCACACA CACATCTCAA
2751 TACACGACCT TCCTTCCACA CCTCTAGACA GACACGCAGA GGATCATGAG
2801 TCCAGGCACG CATTCAAATA CACACAGTTT TAAAAAATTT TTTTTAAAAG
2851 AAAAGAAAAA CTCAAATACA GTTTAGCTGG GCTTGGTGGC TCACGCCTGT
2901 AATTGCAACA CTTTGCGGGG CTGAGGCGGG AGGATTGCTT GAGCCCAGGA
2951 GTTCCAGACC AGCCTGGGCA ATGTAGTGCG GCTCCATCTC TACTAAAAGT
3001 AAAAAAAGTA ACCAGGCATA CTGGTGCACA CCTGTAGTCC CAGCTACTCA
3051 AGAGGTTGAG GCGGGAGGAT CGCTTGAGCC CAGGGGTTCG AGGCTGCAGT
3101 GAGCTGAGAT GGCGCCACTG CGCTTCCAGC CTGGGGGACA GGGCAAGACT
3151 CTGTCTCTAA AAAAAAAAAA ATACAGTCTA TCCAACACAC CCATGGACGG
3201 ACAGCTGAGC ACTCACCTCC CAGCCCTTGC TCTCCGGCAC CGTATGGCTG
3251 ATAGCATCCC CCACCCCCCA GAGCAGTGCT GGTGGAAAGC ATTCCTGAGG
3301 GCCTGGACTT CCCCAATGCC TCCACGGGGA ACCCTTCCAC CAGCCAGGCC
3351 TGGCTGGGCC TGCTCGCCGG TGCGCACAGC AGCCTGGACA TCGCCTCCTT
3401 CTACTGGACC CTCACCAACA ATGACACCCA CACGCAGGAG CCCTCTGCCC
3451 AGCAGGTACC TGCAACCTTG GCCCTGGCCG GCAGCAGGGG CAGGGGGTGG
3501 GAGGCAGCGG GGGCTGTGGG GAATGAAGGG GTTTCTCCTG CAGCCCAGGA
3551 GACAGAGGGG TGTGTCTCAC ACAGCAGATT GGACACAGGT GTTTGCAAGC
3601 AGCTGTCGTC ACGTGGCTCT CTGGACTGGG GGCGTTTGTC ACGGTCATCT
3651 GTAGGCCTCT GAATGTCAGG GTGCGGGTTT GGTTACAAGG GATTATTAGG
3701 CTGGCAGATG TCACTCACCC ACAAGCTGTC CTGACCCAGT CACACAAAGA
3751 AAGGGAAGAG TGGAGTAATT AACAGCCCAG CCTCAAGACA GGGGCCACCT
3801 CCCAGCTGTG TGACCCCAGG CAGGCCACCT CTTCTCTCCA GCTTCAGTTT
3851 CTTTATCTGT AAAATGGGGC AATTTATAG CACCTGCTTC TTAGGGCTCT
3901 TGTGAGGATG AAATGGACTA ATCCATGCAA ATTTTAGCAC AGTGCCTGGC
3951 ACAGAGTCAG CCTTTGTGAG TCTGCTGTTA CTATATATCC TGGTATGGTC
4001 TGCAGACAAA CTTAAAGAAC ATAAAAGCTT CACAATTTGA AAAGGAACAG
4051 CCTACATGGA TAACCTCTTC CATTGAAAAA CCATGAATTT GTTCCTTCTG
4101 TTTTCTTCTC CCTACTGGCT CTTTTTGTGA GAAGTTGTCT TAAAACTTAA
4151 CTAAAATTAC AAGGCTCCTT AAGAACTGCC TGAAAAAAAT AATTATGGCC
4201 AAGTGTGGTG ATTCACACCT GTAATCCCAG CACTTTGGGA GGCCTAGACA
4251 GGAGGATCAC TGGAGCCCAA GAGTTCGAGA CTAGCCTGAG CAACATAGTG
4301 AGACCCGCCC CCACCCTCCC CTCAACCATC TCTACTAAAA ATAAAAAAAA
4351 ATTAGGAGGG TGTTGTGGTG CATGCCTGCA GTCTCAGATA CTCAGGAGAT
4401 GGAAGGAGGA GGATGGCTTG AGCCCAGGAG TTGGAGGCTG CAGCGAGCCG
4451 TGATCATGCC ACTACACTCC AGCCCAGGCA ACATAGCAAG ACCCTGTCTC
4501 AAAAAAAAGA AAAAGAAAAA GTAATAATAA TAATTACAAA AGTTAAAAAC
4551 CAAAGCCAGG CATAGTGGTA CACACCTGTG GTCCCAGCTA CTTGGGAGGC
```

FIGURE 3B

```
4601 TGAAGCAGGA GAATGACTTG AGCCTAGGAA TTGGAGGCTG CAGTGAGCTG
4651 TGATCATGCC ACTGCACTCT AGCCTGGGCA ACATAGTGAA ACCCTGTCTC
4701 TAAAAAAAAA TTTTTTTATG TTAAAAAACC GTATGAGCTC CCACTCCCTG
4751 CTGGCTCCCT CTAAAGTGGT TTAAAACACA GATGTAGGAG GCAGATGGTC
4801 TGGGTTCAAA TCCTGCTCCA TAGCTGGATG TGGTGGTGCA CTCCTGAGGT
4851 ACTAGCTACT TGGGAGACTG AGGCAGGCGG AATGCTTGAG CCCAGGGATT
4901 GAAGATCAGC CTGGGCAACA TAGCAAGTCC CTGTCTCAAC AAACAAACAA
4951 ACAAAAAAAC AAAAACAAAA TCCCACTCCA CTACTGAGTT CTCTGTGGGG
5001 ATTATAATTA AACCAGCCTC ACTGGGTTGT GAGAATTCAG TGAGTTCGCT
5051 GAGAAGAGGC CTAGAACAGG GCCTGGCACA CAGTAGGTTC CAGGGCATCC
5101 TTGACTGTTG CTGTTGTTGG CATCATCGTG CCTCACCCGA TACCTTCCAG
5151 GACCCCCTGC CTGAGCCTCG CCCCCACCAT ACTGGGAGAT GCCTGGAGGC
5201 CCTGCCTTGA TGCTGAATTT TGAGAAAGTC CCTGGAGGGG CAGGAGGGGT
5251 CAGGAGGACT TGGAGGGGGA TCACAGGGCA ACTAATTATT AAAGCAGATA
5301 AAGATGTTTA AAACAGATAA GGAAGTCTTT TAATATTTTA ATCTGTAAAG
5351 TCTTTAATCT ATGCAGGCTA ATGTAAAGTC TGTTTACTCC TAATCATGTC
5401 TCAAAATAAC TCCACCGGGC ATTACCTTGT GGGGTTGGAG AGCTGGCTGG
5451 TCCAGCCCCT CAGAAGCTCT CCCCTCCCCG CAGGGTGAGG AGGTCCTCCG
5501 GCAGCTGCAG ACCCTGGCAC CAAAGGGCGT GAACGTCCGC ATCGCTGTGA
5551 GCAAGCCCAG CGGGCCCCAG CCACAGGCGG ACCTGCAGGC TCTGCTGCAG
5601 AGCGGTGAGC TGGGGCCCAA CTGGGGCTGG TCTGGGCCTG GGGGTACCCA
5651 GCCTGGCCCC TGATCTCTGC CCCTGCTGGT CACAGGTGCC CAGGTCCGCA
5701 TGGTGGACAT GCAGAAGCTG ACCCATGGCG TCCTGCATAC CAAGTTCTGG
5751 GTGGTGGACC AGACCCACTT CTACCTGGGC AGTGCCAACA TGGACTGGCG
5801 TTCACTGACC CAGGTCTGTC TGCACCCTGT CTACCTTCCT TCCAGGCCAC
5851 TCCCTGCCCC ACAGGGCACC CAGCCTCCGA CTGCATCCCT CACTCAATCC
5901 AGAGTCCTCT CCACCCATTC TCTGTAATGG CTTCCTTCTT GCCTCCTACC
5951 AGGCCTCCCT AATCCAAGCC ATGCACGGTG GCTCACACCT ATAATCTCAA
6001 CACTTTGGGA GGCCAAGGTG GGAGGATTGC TTGAGCCCAG GAGTTGGAGA
6051 CCAGCCTGGG CAACATAGTG AGACCCCATC TCTACCAAAA AAAAAAAAAT
6101 AAGCCCGGTG TGGTGGCACA CACCTCTGGT CCCAGCTCCT TGGGAGACTG
6151 AGGTGGGAGG ATCACTTGAG CCCAGGAGTT TGAGGCTACA GTGGGTTGTA
6201 TTCATGCCAC TGCACTCCAG CCTGAGTGAC AGAGTGAGAC CCTGTTACAA
6251 AACAAAGAAT CCCTAAATGG AGCCCTCTAC TGCCCTCCCC CTGCTCCTGG
6301 AAGCCTGGGG CTCCCTCTGA TCCCCAATTG CAGCTACCAG CCCCTCTACA
6351 TGGCATTCAA GAACCTGCGC ACCCATTTGA TCTTCATTGT ACATCTCTGT
6401 GTGCCTGCTC TAAGTCCAGC CCTATCCTGG GTAATGTTGG GAACATGGTG
6451 GTAACAGATG GACCTCATGG AACTCCAGCC CAATGCAGA CTGGCCTGTC
6501 ACCTGACAGT GACAGCCCAG AGGGGTCAGG GCCGGGGTTG GGGAGACACA
6551 GGCAGAGGGT CAGGGCCAGG ATGGAGGGAA CAGAGGGCTG TGGAAGCTCA
6601 GAGACCCCAA CCTGGGGCAT TGGAGGGTTT CCCAAAGGAG GTATAACTAA
6651 TCTGATCCCT GAAGGATAGG GAGGAATTAG CGCAAGATGG AACAGGAAAC
6701 AGCTTGGGCA ATGAGGTGAA GATAAGACAG GACAATAACT CATGAATTCA
6751 TTTCCTCAAC AGATAGTTCC CCTAACCTTT AATCTCAGCA ATTATGCAGG
6801 GAGATGCTGT AGATATAGCT GTGACTGAGA CATCCCTAGT GCCTGTCCTC
6851 CCAGCCCAAT GGAAGACCA GTTTGTCACC AGAAAGAATG AGGAGGGAAT
```

FIGURE 3C

```
6901 CCCAAGGGAC TGTGAGAGCC CAGAGGAATG CCTGGTGCAG GCTGGGTAGT
6951 CACGGGAGGC TTCCTGAAGG AGGCAACATG TCAGCCTAGA CCTAAGAATG
7001 AGTAGAAGCT AGCTCAGTGG AGGGTAGAAG CAACAGCAGA TTGCAAACGT
7051 TCAGGAAACC TGGAGCTTTG GAATAACTGA TTTTCATCAA AACTTAAGTT
7101 GATAATCATT CTAGGACTTT AGCTATTGGA GCTGGGGTGG AGGGGGTACT
7151 GTGGGACAGG GGGAAAGACA GAGACCAGAC TGGGGAGTGT CCCTGTCATC
7201 TGTGAGCACT AGGCCGCTAT CGCTGAGCTC AGCACTGCCC TCCTACAGGT
7251 CAAGGAGCTG GGCGTGGTCA TGTACAACTG CAGCTGCCTG GCTCGAGACC
7301 TGACCAAGAT CTTTGAGGCC TACTGGTTCC TGGGCCAGGC AGGCAGCTCC
7351 ATCCCATCAA CTTGGCCCCG GTTCTATGAC ACCCGCTACA ACCAAGAGAC
7401 ACCAATGGAG ATCTGCCTCA ATGGAACCCC TGCTCTGGCC TACCTGGCGG
7451 TGAGTCTGGG GCAAGTGGGG CCTGTCATGT CCCAGCCCCA TGCCGTCACT
7501 CACAGCCTCC ATCTGTCCCT GTTTGGTGAT GACAGGGAGG GCGTATCCTG
7551 ACCATCAGTT CTCACCCCAG CTCATTCTGC TTGGTCAGGG GCCTGGAGTA
7601 GTTCCCAACA TCCCTCGGCC TCTATTTCAG TTAGAAAATG GGTATTGTTT
7651 CCAACCTGTT AGGGCTGCTG GGAGAGGTAC CCTGGGTTCA TGCACACCAA
7701 ACCTTTGGTG CTCTATATCA TCCAGTATAG CCACAGGTGG CTCTTTCAGT
7751 TTAAGTTAAT TAAATGCAAT TAACAATTCA GGCCAAGTGG GGTGGCTTAT
7801 GCCTGTAATC CCAATACTTT GGGAGGTTGA GGTGACAGGA TCACTTGAGG
7851 CCAGGAGTTT GAGACCAGCC TGGACAACAT AGCAAGACTC CATCTTTACA
7901 AACAAACAAA CAAACAAACA AAACTAGCTG GGTTGGGTTG TGCATGCATG
7951 TAGTCACAGC TACGCAGGAG GCTGAGGCAG GGGGATCACT TGAGCCCAGG
8001 AAATCTAGGC TGCAGTGAGC CATGATCACA CCACTGTACT CCAGCCTGGG
8051 TGACAGCCTG TTTCAAAAAA AAATTGTTTC AAGCCAGGCA TGGTTTCTCA
8101 TCCCTGTAAT CCCAGCACTT TGGGAGGCCA AGGCCAAGAT GGGAGGATCA
8151 CTTGAGGCCA GGAGTTCATG ACCAGCCTGG GCAACATAGG GAGACATCAT
8201 TTCTTTCTAT TTTTTTTTTT TTTTGGTCTT ATTATTTATT GTTCTAGATA
8251 GGATACCCAA GAACTAGGGA GACACCATTT CTACAAAAAC ATAATATTAA
8301 TTAAAATTAG CCGGGTGTGG TTGTGTGCAC CTGTAGTCCC TGGGGAGGCT
8351 AAGACAGGGG GATCACTTGA GCCCAGGAGT TTGAGGCTGC GTGAGCTGAT
8401 TGTACCACTG CACTCCAGCC TGGGCAAGAG GCTGTTGCCC TGTCTCCAAA
8451 AAAAGAAAAA ATTCAGTTCC TCATGCAGTA GCCACATTTC ATATGCTCAG
8501 TAGCACCTGT AGCAAGTGAC CACCATATTG GACATTTCCA TCACTGTGAC
8551 AGGCTCTGTT GGACAACACT GGCTCTCGCC ATGGCAGATA CTGATCACTC
8601 TGGACAAGGC ACTGATGTTT CTAGCTCTTG ATAGTTTCAC TAGTTGAGGC
8651 AGGCAACCCA GGTCTCCCTA GGTCCCCCTG AGCAAGTTAC CTGTCCAAGC
8701 CCAGAGTCAT CGTGGAAGGC ACAACCCTAA GGCGTGGACG TAGGGAAGTG
8751 TGACTCATTG GGGTCTTTCA CTACAAGGGC CTCCCGCAGG GGATCAAGGC
8801 TCTCCTCATT ACCACTTCCC CTTTTAGAGC CTCAGTTTCC TTGTCTCTTG
8851 AGCATTAAGG AAGATGGGGG GCCAGGCACA GTGGCTCATG CCTGTAATCC
8901 TAGCATTTTG GGAGTCCAGG ATGGGCGGAT CACTTGAGCT CAGGGGTTGG
8951 AGACCAGCCT GGGAAACGTG ATGAAACCCC ATCTCTACCA AAAATACAAA
9001 AATTAGCCTG GAGGGGTGGC GGGCACCTGT AATCCCAGCT ACTCGGGAGG
9051 CTGAGGCAGG AGAATCACTT GAACCCAGGA GGTAGAGGTT GCAGGGAGCC
9101 GAGATTGCAC CATTGCCCTC CAGGCTGGGT GACAGAGTGA GACTCCACTT
9151 CAAAAAAAAA AAAGGGGGGG GAAGCGGGGG AGCGGGGGAA CTGGGAAGAG
```

FIGURE 3D

```
9201 GGCCTGGTGA GGCACTGGGC ACCCGAGGGG TTCCCAGTCA AGGCAGGCTG
9251 TGAGCAAATC AGGGAAGAAA GTGACTCGAG GCTGGGCACA GTGGCTCACG
9301 CCTGTAATCC CAGCACTTTG GGAGGCCTAG GCAGGTGGAT TGCCTGAGGT
9351 CAGGAGTTCG AGACCTGCCT GGCCAACATG GTGAAATCCC ATCTCCACTA
9401 AAAATACAAA AAAATTAGCT GGCTATGGTG ATGTACGCCT GTAGTCCCAG
9451 CTACTTGGGA GGCTGAGGCA GGAGAATCGC TTGAACCCAA GAGGCAGCAG
9501 AGGTTGCAAT GAGCTGAGAT CATGCCACTG CACTCCAGCC TAGGAGACAG
9551 AGCAAGACTC CATCTCAAAA AAAAAAAAAA AAAAAAAGAC TTGAGCAGAG
9601 GTCCTCAAAC TGAGCATGCC CCAGAATCAG CTGGGCGGGC TTGTTAAAAC
9651 CCAGATTCCT GGACCCCACC CCAGCACTCT GATTCAGTAG GCCATGTGCA
9701 GTGAGGCCCA GGAATTTGCA TTTCTAACAA GTTCCCAGGT GATGCTGTTG
9751 CCGCTGGATC AGGGACCTTA CGTTGAGAAG CACTGGGTTA GAGCGTAAAT
9801 TCTGGAACCA GACAGCCTGG GTTCGAATCC TGGCTCCATT TATCTGCTGT
9851 GTGACTTTAA GTAAGTCACT TACCCTCTCT GAGCCTCAGT TTCCTCACAT
9901 GTGAAATGGA TGTGGTGATT GACCCTCTTC TTCATGGAGG CTGAGGATTT
9951 GGTGAGATCC ACAGTACCTG GCTTGTGGTG AGCTGTCCGT ATGTGGGTC
10001 CGTTGTGACG ATGACCCTGG CAGGGCACAT GTCTTAACTG TCCCCTCGCC
10051 CTCAGAGTGC GCCCCACCC CTGTGTCCAA GTGGCCGCAC TCCAGACCTG
10101 AAGGCTCTAC TCAACGTGGT GGACAATGCC CGGAGTTTCA TCTACGTCGC
10151 TGTCATGAAC TACCTGCCCA CTCTGGAGTT CTCCCACCCT CACAGGTACT
10201 GCTGGGTGTG GAGATAGGGA GCCGCTGCAG TTGGCCAGGA GACGGGAGAG
10251 GGAATCATGG AGACCAGAAA GCTGGTGGGG GCTCCAGGCA AGGGGACAGA
10301 TGGAAGAGAA GCTGCAGGGA GAGACAGTCA CCAGGAGGTG ACCGGAAGAA
10351 GGTATCTAGG CACTTGAGAC AGGAGAAAGA GAGATTACAG AGGAGACAGG
10401 GATGAGGTTT CAGGACAAGG TTTGAGGGAA CAGAGAAAAG GATGAGAGGG
10451 CCGGGCGTGG TGGCTCACGC CTGTAATCCC AACATTTTGC GGGGCTGAGG
10501 TGGGTGGATC ACTTGAGGTC AGGAGTTCAA GACCAGCCTG GCTAACATGG
10551 TGAAATCCCA TCTCTCCTAA AAATACAAAA ATTAGCCGGG CGTGGTGGCA
10601 CGTGCTTGTA ATCCCAGCTA CTTGAGAGGC TGAGGCAGGA GAATTGCTTG
10651 AACCTGGGAG GTGAAGGTTG CAGTGAGTTG AGATCGCGCC ACTGCTCTCC
10701 AGCCTGTGCG ACAGACAGAG CAAGACTCTG TCTCAAAAAA ACAACAAAAA
10751 AAAAGAGAAG GCTCAGAATA TTGGGGTTGA GGGCAGGAAG CCTGAGGCAG
10801 GGGTGCAGGA TGTGGGATTT GGGGAGGTAG GAGGCATGGG CTGGAAACAG
10851 GATGAGGGGC TTGGGGGATG GGGACTAAAA GTATTTGGGT TTAGGGTAGC
10901 AAGCTTGGGG ATTTGTGATC CTGGGATAAG AAGGATAACA ACCGGCCGGA
10951 CGTGGTGGCT CACACCTGTA ATCCCAGCAC TTTGGGAGGC TGAGGCGGGT
11001 GGATCACGAG GTCAGGAGAT CGAGACCATC CTGGCCAACA TGGTGAAGCC
11051 CCGTCTCTAC TAAAAATACA AAAAATTAGC CAGGTGTGGT GGCAGGCGCC
11101 TGTAGTCCCA GCTACTTGGG AGGCTGAGGC AGGAGAATCG CTTGAACCCG
11151 GGAGTCGGAG GTTGCAGTGA GCCAAGATCA TGCCACTGCA CTCCAGCCTG
11201 GGCGACGGAG CGAGACACCT TCTCAAAAAA AAAAAAAGA AAAGAAAAAA
11251 AAAAGAAGG ATAACAACCA TACCCACTGC AACATCCAGG TGGATGATGG
11301 CACTTGTGGG GCTCAAAGAA GGTATTCTAG GGGCAGTAGA TAAGACAGTG
11351 GGTCCAGGCA TGGTGGCTCA CGCCTGTAAT CCCAACACTT TGGGAGGCCG
11401 AGGCGGAAGG ATCCCTAGGA GTTTGAGACC AGCCTGGGCA ACATAATGAG
11451 ACCCCGTCTC TATAGAAAAA TTGGAAGATT AGCCCAGTGC GGTGGCACTC
```

FIGURE 3E

```
11501 ACCTGCAGTC CCAGCTACTC AGGAGACTGA GGCAGGAGGA TCACTTGAGC
11551 CCAGGAGTTG GAGGCTGCAT TGAGCTATGG TCGTGCCACT ACACTCCAGC
11601 CTGGGTGATA GAGCAAGAAC CTGTCTCAAA AAGAAAAAAA AGAGGATGGA
11651 CCGGGCACAG TGGCTCACGC CTGTAATCCC AGCACTTTGG GAGGCCAAGG
11701 CGGGCAGATC ACCTGAGGTC GGGAGTTCGA GACCAGCCTG ACAAACATGG
11751 AGAAACCCCG TCTCTACTAA AAATACAAAA TTAGCCAGGC GTGGTAGCGC
11801 ATGCCTGTAA TCCTAGCTAC CCGGGAGGCT GAGGCAGGAG AATCGCTTGA
11851 ACCCAGGAGG CAGAGGTTGC AGTGAGCCGA GATTGTGCCA TTGCACTCCA
11901 GCGTGGGCAA CAAGAGCGAA ATTCCACCTC AAAAAAAAAA AGAAAGAAAG
11951 AATAAAAGAG GATGACAACA CTGGGTTTTG GGAGCAGGA ATGGAGCCA
12001 CAGCCAGGAA GAGGAAATAG GGATGTGGGA TTTATGGAGA CAGGAACAGG
12051 GTCTGGGAGC CAGCGATGAG GAAGTCCTCT CAATAGCTAA AGCAGGGCCC
12101 AGGCTTGGTT CCCCAAAGCT GAGGGCAAAG CCTGTGGACA CAGCCGCCCT
12151 CTGCATCCTG CCCCACCTCC TATACACCCG TCCTCAGGTT CTGGCCTGCC
12201 ATTGACGATG GGCTGCGGCG GGCCACCTAC GAGCGTGGCG TCAAGGTGCG
12251 CCTGCTCATC AGCTGCTGGG GACACTCGGA GCCATCCATG CGGGCCTTCC
12301 TGCTCTCTCT GGCTGCCCTG CGTGACAACC ATACCCACTC TGACATCCAG
12351 GTGGTAAGTA CTGCCCCAAG CCACCCCTTG GCCCCTGTGT GGGGCAGTCC
12401 TAGGGACACA GCCCTCATGG GACTCGTCTG TCAATGACAA GGGCAGCCCA
12451 GAGTGAGCCC TGTCACTGTG GGGAAACCAT GGGTCAGGGC CAGGGTCATG
12501 GGGCACAGGG AGAGGGGCCA GGACCGGGAT GAGGGGGCAC AGGCAGAGGG
12551 GTTGGGACCG GGATGGGGGT GCAGAGAGAG GTGTTGGGAC CAGGAATGGG
12601 GACATGGGCA GGTAGAGGGG TCAGGGCTGG GATTGGGAGC ACAGGCAGAG
12651 GGGTCAGGGC TGGGATGGGG AGGCACAGGC AGAAGGGTCG GGGCCGGGTT
12701 GGAGGGCACA GGGAGAGGGG TTAGGGCCAG GGTTGGGGGC ACAGGCAGAG
12751 GGGTCGGGGC CAGGATGGAG GAGGCCCAGG CAGAGGGGTG AGGGCTTGGG
12801 GTGGGGGGCA CAGAGAGAGG GTTTGGGACC AGGACTGGGG GAGTGGGCAG
12851 GTAGAGGGGT CGGGGCTGGG GTTGGGGGCA CAGGCAGAGG GGTCAGGGCT
12901 GGGATGGAGG AGGTACAGGC AGAGGGGTCA GGGCTGGGAT GGGGGGGCAC
12951 AGGCAGAGGG GTCAGGGCTG GGATGGAGGA GGCCCAGGCA GAGGGGTCAG
13001 GGCCCAGGGT CGGGGGGCAC AGGCAGAGGG GTCAGGGCTG GGGTGGGGAT
13051 GCCCAGAGGA AGCCTCTGCC CTAGCGGGAA GGGCCAAGGA AGATGTTCTG
13101 GAAATGGGGG CATCTGAGAT GAGACCTCAG GAATGAACAG GAGCCATTCT
13151 GCCGGGAACA GTGTTTTGCA AATGAGACCA CCGGGGCCTC CCTTTCAGCT
13201 TTCGTTCTCA GAGGGCCCCT CCACCTGGCC CTGTTCTGGC CCCCGAGGAT
13251 TCTGTGGGAA GCAGTGGAGT CCCACAGATC TCGCTCCACA CTCTGCTCCC
13301 TGATCCCGGG GCTCCTCCGA CTCCCCCTGC CTCTCACACT CCTTCCCATC
13351 CTCCCCTCCC ACTCAGAAAC TCTTTGTGGT CCCCGCGGAT GAGGCCCAGG
13401 CTCGAATCCC ATATGCCCGT GTCAACCACA ACAAGTACAT GGTGACTGAA
13451 CGCGCCACCT ACATCGGTGA GTGTCTTGAG CACCACGGGG CGCTGAAGAA
13501 GAGGGGGTTC AGACACCAGG GGCGGCCCCC CGAGGGTGCC CTTATGCTCC
13551 ACCCATTCCT CTCTAGGAAC CTCCAACTGG TCTGGCAACT ACTTCACGGA
13601 GACGGCGGGC ACCTCGCTGC TGGTGACGCA GAATGGGAGG GGCGGCCTGC
13651 GGAGCCAGCT GGAGGCCATT TTCCTGAGGG ACTGGGACTC CCCTTACAGC
13701 CATGACCTTG ACACCTCAGC TGACAGCGTG GGCAACGCCT GCCGCCTGCT
13751 CTGAGGCCCG ATCCAGTGGG CAGGCCAAGG CCTGCTGGGC CCCCGCGGAC
```

FIGURE 3F

```
13801 CCAGGTGCTC TGGGTCACGG TCCCTGTCCC CGCGCCCCCG CTTCTGTCTG
13851 CCCCATTGTG GCTCCTCAGG CTCTCTCCCC TGCTCTCCCA CCTCTACCTC
13901 CACCCCCACC GGCCTGACGC TGTGGCCCCG GGACCCAGCA GAGCTGGGGG
13951 AGGGATCAGC CCCCAAAGAA ATGGGGGTGC ATGCTGGGCC TGGCCCCCTG
14001 GCCCACCCCC ACTTTCCAGG GCAAAAAGGG CCCAGGGTTA TAATAAGTAA
14051 ATAACTTGTC TGTACAGCCT GTGCCTGACT GAGTGGTGTG AGATGGGGTG
14101 CAGGGGTAGG GGACAGCTGG CATGGGCCTC TGGTGGGGAC ATCTTTTTGT
14151 GCTGAGCCCT CAACATGTCA CTGGCATGTG CTGAGCCCTC AGTGTGTGAC
14201 CAGTGTGGGT TAGCATGTAC TGAGCCCTCA GCATGTGCTG CATGGGTTG
14251 GCATGTGCTG AGCCCTTAAC ATGTAGTGTA CATGGGCTGA CCTGTGCTGA
14301 GCATGCAGCG TGCCACCCTG TGGCCCGGCA TGGACTTAGC ACTCATGTAG
14351 CCAGCATGGG TATGTGCTGC AGAGAAGCAT GTTCCCAGAT TGATCAGCAG
14401 GGACCAAACC ATTGCCACAT CCCAAGGGTG AACAAGCATG CTGAGCACC
14451 AGAGTGTGCA CCAAGTGTGA ATTTAGGCCT GCCAAGTGGA TTTACACCCA
14501 GCACGTCCCA AATGTGGGTG AGTGCATGCC AACCCTGTAA ACATGTAGGA
14551 AGGACAGGTC AACAGACAAG GAGACCCCAG CATCCGGCAA ACTTGATTAA
14601 CACATACTGA ACACAGCATG TTCTGAGGGT GGATTCCCAA CACGCCAAGC
14651 ACATAGCGTA TTTAGGACAA GGGTTAGTCA ACCAAGCACA GCTTTTCCCT
14701 CCTAGTGTGA CAGCAGCCCA GGCTCCCGCC TAAGCCAGTG GTCAGCTGGG
14751 CCCAGCATCG CAGAGCAAGT CACTGGGTGC CAGCCTGGAG CCCCCATTCC
14801 CCCCAGGGCC AGTCCAAGCC CCAGGCAGTG AGAGCAGGCT TGAAGCAGGA
14851 CTGCTGAACA GTTCTATATT GAAATAGACA GAGGCAGCAG GGCCAAGGGC
14901 GAGCGCAGGG CCAGCGGGGT GCAGCCCCCT TTCCTGCTGT CCTTCTGGCC
14951 AAGGAGCATG GGCCAGACTC CAAAGCCCTG CTGTGTTTAG GAGAGGTGTG
15001 CAGGCACGCA CCGCACCGCA GACGGGGAAT GAGAATTTCT GGATAACTAT
15051 CTTTCTGTAA GAATAATTTG TGGGTTCAGG AGATGGCTCT GAGGAGCAGT
15101 TCAGGTTGGG AGGGAATGCC AGCCCAGCTA GCGCAGCCCC CAGTGATGGG
15151 CAGGGGTGGA ATCACCATCA GTGGTGCCCG GTGACATGCT GGAGGAAGCT
15201 GGTGGCCCCC CGGGGTGGAC CATGCTGGTG GGAGCGGCGG GGTGGGAGCC
15251 CCTGAGCCCG TGGGCCCCTG ACGCTCTCCA GGGTGCAGTC TGGCTCACTC
15301 AGCCATTCTC CAGGACAGCT GCTGGGGTCG AAGAGCTCAG GGTCTGGCCT
15351 CTGTGGGGGA AGAGAGAGGG GCATCAGCCA AGCAGTGTTA GTGTATTAGT
15401 GTCTGCTGAG CCTCTGTCAC CTCCTCCTGA TGAGGGTGAG CATGTGCTAG
15451 GGTCTTACCA GTGCTGGGCC TTTATTGCCC CTTTGTAGTG ATGTGATGAC
15501 AGCTCACTGC AGCCTCGACC TCCCTGGCTC AAGTGATCCT CCCACCTCAG
15551 CCTCCTGAGT AGCTGGGACT ACAGGTGCAT GCCACCAAAA CCAGCTAATA
15601 TTTCTAATTT TTTGGTGCAG ACGGGATCTC ACTATGTTGC CCAGGCTCTT
15651 TATCAAGCTT CTTATAAGTA GATTACTGTG CCCTGAGTTT TTGTCACAGC
15701 CTGGAAGTAG CTGAGTAAGT GCTGAGCCTT ATCATATCTT GACGGTATTA
15751 GGTGTGTGCT GAGCCTCCTA AGTCCCTAAT TGTATCCTGA ACATGGGTGA
15801 GTGTGTGTTG AGCCTCCTCA CACACTAATC ATATCCTGAG CACGGGTGAG
15851 TGTGTGCTGA GCCTCCTCCC ACCCTAATCG TATCCTGAAC GCACCCGGCT
15901 CACCTCAGCT TCCATGGTCA TGTTGTCAAT GTTGGGCCCA TCCTCATCTC
15951 GCTGCAGGAT GGCCAGTGGC TCAGCAGAGG CCCCGAGATG CTCTCCTTCC
16001 TCCCAGCTGC TGCCCCGGCA GGGCCTGTCA TCCTCAGGCG AGACCTGGCT
16051 CAGCCGAATG AGG (SEQ ID NO:3)
```

FIGURE 3G

FEATURES:
Start: 2060
Exon: 2060-2086
Intron: 2087-2348
Exon: 2349-2491
Intron: 2492-3271
Exon: 3272-3455
Intron: 3456-5483
Exon: 5484-5604
Intron: 5605-5685
Exon: 5686-5813
Intron: 5814-7248
Exon: 7249-7449
Intron: 7450-10055
Exon: 10056-10195
Intron: 10196-12187
Exon: 12188-12353
Intron: 12354-13366
Exon: 13367-13466
Intron: 13467-13566
Exon: 13567-13751
Stop: 13752

CHROMOSOME MAP POSITION:
Chromosome 2

ALLELIC VARIANTS (SNPs):

| DNA Position | Major | Minor | Domain | Protein Position | Major | Minor |
|---|---|---|---|---|---|---|
| 3011 | A | G | Intron | | | |
| 9795 | G | A | Intron | | | |
| 10389 | A | G | Intron | | | |
| 11399 | C | T | Intron | | | |
| 13607 | C | T G | Exon | 417 | A | A A |
| 13826 | C | T G | Beyond ORF(3') | | | |
| 13834 | C | T G | Beyond ORF(3') | | | |
| 14745 | G | A | Beyond ORF(3') | | | |
| 15083 | A | T | Beyond ORF(3') | | | |

Context:

FIGURE 3H

DNA
Position
3011   ATCTTCCACCCACATCTGTGGACCCACACACACATCTCAATACACGACCTTCCTTCCACA
       CCTCTAGACAGACACGCAGAGGATCATGAGTCCAGGCACGCATTCAAATACACACAGTTT
       TAAAAAATTTTTTTTAAAAGAAAAGAAAAACTCAAATACAGTTTAGCTGGGCTTGGTGGC
       TCACGCCTGTAATTGCAACACTTTGCGGGGCTGAGGCGGGAGGATTGCTTGAGCCCAGGA
       GTTCCAGACCAGCCTGGGCAATGTAGTGCGGCTCCATCTCTACTAAAAGTAAAAAAAGTA
       [A,G]
       CCAGGCATACTGGTGCACACCTGTAGTCCCAGCTACTCAAGAGGTTGAGGCGGGAGGATC
       GCTTGAGCCCAGGGGTTCGAGGCTGCAGTGAGCTGAGATGGCGCCACTGCGCTTCCAGCC
       TGGGGGACAGGGCAAGACTCTGTCTCTAAAAAAAAAAAAAATACAGTCTATCCAACACACC
       CATGGACGGACAGCTGAGCACTCACCTCCCAGCCCTTGCTCTCCGGCACCGTATGGCTGA
       TAGCATCCCCCACCCCCCAGAGCAGTGCTGGTGGAAAGCATTCCTGAGGGCCTGGACTTC 9795   CAGCAGAGGTTGCAATGAGCTGAGATCATGCCACTGCACTCCAGCCTAGGAGACAGAGCA
       AGACTCCATCTCAAAAAAAAAAAAAAAAAAAAAAGACTTGAGCAGAGGTCCTCAAACTGAG
       CATGCCCCAGAATCAGCTGGGCGGGCTTGTTAAAACCCAGATTCCTGGACCCCACCCCAG
       CACTCTGATTCAGTAGGCCATGTGCAGTGAGGCCCAGGAATTTGCATTTCTAACAAGTTC
       CCAGGTGATGCTGTTGCCGCTGGATCAGGGACCTTACGTTGAGAAGCACTGGGTTAGAGC
       [G,A]
       TAAATTCTGGAACCAGACAGCCTGGGTTCGAATCCTGGCTCCATTTATCTGCTGTGTGAC
       TTTAAGTAAGTCACTTACCCTCTCTGAGCCTCAGTTTCCTCACATGTGAAATGGATGTGG
       TGATTGACCCTCTTCTTCATGGAGGCTGAGGATTTGGTGAGATCCACAGTACCTGGCTTG
       TGGTGAGCTGTCCGTATGTGGGGTCCGTTGTGACGATGACCCTGGCAGGGCACATGTCTT
       AACTGTCCCCTCGCCCTCAGAGTGCGCCCCCACCCCTGTGTCCAAGTGGCCGCACTCCAG 10389  ACTCCAGACCTGAAGGCTCTACTCAACGTGGTGGACAATGCCCGGAGTTTCATCTACGTC
       GCTGTCATGAACTACCTGCCCACTCTGGAGTTCTCCCACCCTCACAGGTACTGCTGGGTG
       TGGAGATAGGGAGCCGCTGCAGTTGGCCAGGAGACGGGAGAGGGAATCATGGAGACCAGA
       AAGCTGGTGGGGGCTCCAGGCAAGGGGACAGATGGAAGAGAAGCTGCAGGGAGAGACAGT
       CACCAGGAGGTGACCGGAAGAAGGTATCTAGGCACTTGAGACAGGAGAAAGAGAGATTAC
       [A,G]
       GAGGAGACAGGGATGAGGTTTCAGGACAAGGTTTGAGGGAACAGAGAAAAGGATGAGAGG
       GCCGGGCGTGGTGGCTCACGCCTGTAATCCCAACATTTTGCGGGGCTGAGGTGGGTGGAT
       CACTTGAGGTCAGGAGTTCAAGACCAGCCTGGCTAACATGGTGAAATCCCATCTCTCCTA
       AAAATACAAAAATTAGCCGGGCGTGGTGGCACGTGCTTGTAATCCCAGCTACTTGAGAGG
       CTGAGGCAGGAGAATTGCTTGAACCTGGGAGGTGAAGGTTGCAGTGAGTTGAGATCGCGC 11399  CCTGTAGTCCCAGCTACTTGGGAGGCTGAGGCAGGAGAATCGCTTGAACCCGGGAGTCGG
       AGGTTGCAGTGAGCCAAGATCATGCCACTGCACTCCAGCCTGGGCGACGGAGCGAGACAC
       CTTCTCAAAAAAAAAAAAAAAGAAAAGAAAAAAAAAAAGAAGGATAACAACCATACCCACT
       GCAACATCCAGGTGGATGATGGCACTTGTGGGGCTCAAAGAAGGTATTCTAGGGGCAGTA
       GATAAGACAGTGGGTCCAGGCATGGTGGCTCACGCCTGTAATCCCAACACTTTGGGAGGC
       [C,T]
       GAGGCGGAAGGATCCCTAGGAGTTTGAGACCAGCCTGGGCAACATAATGAGACCCCGTCT

FIGURE 3I

```
        CTATAGAAAAATTGGAAGATTAGCCCAGTGCGGTGGCACTCACCTGCAGTCCCAGCTACT
        CAGGAGACTGAGGCAGGAGGATCACTTGAGCCCAGGAGTTGGAGGCTGCATTGAGCTATG
        GTCGTGCCACTACACTCCAGCCTGGGTGATAGAGCAAGAACCTGTCTCAAAAAGAAAAAA
        AAGAGGATGGACCGGGCACAGTGGCTCACGCCTGTAATCCCAGCACTTTGGGAGGCCAAG
13607   CGGGGCTCCTCCGACTCCCCCTGCCTCTCACACTCCTTCCCATCCTCCCCTCCCACTCAG
        AAACTCTTTGTGGTCCCCGCGGATGAGGCCCAGGCTCGAATCCCATATGCCCGTGTCAAC
        CACAACAAGTACATGGTGACTGAACGCGCCACCTACATCGGTGAGTGTCTTGAGCACCAC
        GGGGCGCTGAAGAAGAGGGGGTTCAGACACCAGGGGCGGCCCCCCGAGGGTGCCCTTATG
        CTCCACCCATTCCTCTCTAGGAACCTCCAACTGGTCTGGCAACTACTTCACGGAGACGGC
        [C,T,G]
        GGCACCTCGCTGCTGGTGACGCAGAATGGGAGGGGCGGCCTGCGGAGCCAGCTGGAGGCC
        ATTTTCCTGAGGGACTGGGACTCCCCTTACAGCCATGACCTTGACACCTCAGCTGACAGC
        GTGGGCAACGCCTGCCGCCTGCTCTGAGGCCCGATCCAGTGGGCAGGCCAAGGCCTGCTG
        GGCCCCCGCGGACCCAGGTGCTCTGGGTCACGGTCCCTGTCCCCGCGCCCCCGCTTCTGT
        CTGCCCCATTGTGGCTCCTCAGGCTCTCTCCCCTGCTCTCCCACCTCTACCTCCACCCCC
13826   CCCCCCGAGGGTGCCCTTATGCTCCACCCATTCCTCTCTAGGAACCTCCAACTGGTCTGG
        CAACTACTTCACGGAGACGGCGGGCACCTCGCTGCTGGTGACGCAGAATGGGAGGGGCGG
        CCTGCGGAGCCAGCTGGAGGCCATTTTCCTGAGGGACTGGGACTCCCCTTACAGCCATGA
        CCTTGACACCTCAGCTGACAGCGTGGGCAACGCCTGCCGCCTGCTCTGAGGCCCGATCCA
        GTGGGCAGGCCAAGGCCTGCTGGGCCCCCGCGGACCCAGGTGCTCTGGGTCACGGTCCCT
        [C,T,G]
        TCCCCGCGCCCCCGCTTCTGTCTGCCCCATTGTGGCTCCTCAGGCTCTCTCCCCTGCTCT
        CCCACCTCTACCTCCACCCCCACCGGCCTGACGCTGTGGCCCCGGGACCCAGCAGAGCTG
        GGGGAGGGATCAGCCCCCAAAGAAATGGGGGTGCATGCTGGGCCTGGCCCCCTGGCCCAC
        CCCCACTTTCCAGGGCAAAAAGGGCCCAGGGTTATAATAAGTAAATAACTTGTCTGTACA
        GCCTGTGCCTGACTGAGTGGTGTGAGATGGGGTGCAGGGGTAGGGGACAGCTGGCATGGG
13834   GGGTGCCCTTATGCTCCACCCATTCCTCTCTAGGAACCTCCAACTGGTCTGGCAACTACT
        TCACGGAGACGGCGGGCACCTCGCTGCTGGTGACGCAGAATGGGAGGGGCGGCCTGCGGA
        GCCAGCTGGAGGCCATTTTCCTGAGGGACTGGGACTCCCCTTACAGCCATGACCTTGACA
        CCTCAGCTGACAGCGTGGGCAACGCCTGCCGCCTGCTCTGAGGCCCGATCCAGTGGGCAG
        GCCAAGGCCTGCTGGGCCCCCGCGGACCCAGGTGCTCTGGGTCACGGTCCCTGTCCCCGC
        [C,T,G]
        CCCCCGCTTCTGTCTGCCCCATTGTGGCTCCTCAGGCTCTCTCCCCTGCTCTCCCACCTC
        TACCTCCACCCCCACCGGCCTGACGCTGTGGCCCCGGGACCCAGCAGAGCTGGGGGAGGG
        ATCAGCCCCCAAAGAAATGGGGGTGCATGCTGGGCCTGGCCCCCTGGCCCACCCCCACTT
        TCCAGGGCAAAAAGGGCCCAGGGTTATAATAAGTAAATAACTTGTCTGTACAGCCTGTGC
        CTGACTGAGTGGTGTGAGATGGGGTGCAGGGGTAGGGGACAGCTGGCATGGGCCTCTGGT
14745   AGCACCAGAGTGTGCACCAAGTGTGAATTTAGGCCTGCCAAGTGGATTTACACCCAGCAC
        GTCCCAAATGTGGGTGAGTGCATGCCAACCCTGTAAACATGTAGGAAGGACAGGTCAACA
        GACAAGGAGACCCCAGCATCCGGCAAACTTGATTAACACATACTGAACACAGCATGTTCT
        GAGGGTGGATTCCCAACACGCCAAGCACATAGCGTATTTAGGACAAGGGTTAGTCAACCA
        AGCACAGCTTTTCCCTCCTAGTGTGACAGCAGCCCAGGCTCCCGCCTAAGCCAGTGGTCA
```

FIGURE 3J

[G,A]
CTGGGCCCAGCATCGCAGAGCAAGTCACTGGGTGCCAGCCTGGAGCCCCCATTCCCCCCA
GGGCCAGTCCAAGCCCCAGGCAGTGAGAGCAGGCTTGAAGCAGGACTGCTGAACAGTTCT
ATATTGAAATAGACAGAGGCAGCAGGGCCAAGGGCGAGCGCAGGGCCAGCGGGGTGCAGC
CCCCTTTCCTGCTGTCCTTCTGGCCAAGGAGCATGGGCCAGACTCCAAAGCCCTGCTGTG
TTTAGGAGAGGTGTGCAGGCACGCACCGCACCGCAGACGGGGAATGAGAATTTCTGGATA

15083   GCCTGGAGCCCCCATTCCCCCCAGGGCCAGTCCAAGCCCCAGGCAGTGAGAGCAGGCTTG
AAGCAGGACTGCTGAACAGTTCTATATTGAAATAGACAGAGGCAGCAGGGCCAAGGGCGA
GCGCAGGGCCAGCGGGGTGCAGCCCCCTTTCCTGCTGTCCTTCTGGCCAAGGAGCATGGG
CCAGACTCCAAAGCCCTGCTGTGTTTAGGAGAGGTGTGCAGGCACGCACCGCACCGCAGA
CGGGGAATGAGAATTTCTGGATAACTATCTTTCTGTAAGAATAATTTGTGGGTTCAGGAG
[A,T]
TGGCTCTGAGGAGCAGTTCAGGTTGGGAGGGAATGCCAGCCCAGCTAGCGCAGCCCCCAG
TGATGGGCAGGGGTGGAATCACCATCAGTGGTGCCCGGTGACATGCTGGAGGAAGCTGGT
GGCCCCCCGGGGTGGACCATGCTGGTGGGAGCGGCGGGTGGGAGCCCCTGAGCCCGTGG
GCCCCTGACGCTCTCCAGGGTGCAGTCTGGCTCACTCAGCCATTCTCCAGGACAGCTGCT
GGGGTCGAAGAGCTCAGGGTCTGGCCTCTGTGGGGGAAGAGAGAGGGGCATCAGCCAAGC

FIGURE 3K

ISOLATED HUMAN PHOSPHOLIPASE PROTEINS, NUCLEIC ACID MOLECULES ENCODING HUMAN PHOSPHOLIPASE PROTEINS, AND USES THEREOF

RELATED APPLICATIONS

The present application is a divisional of U.S. application Ser. No. 10/020,121, filed on Dec. 18, 2001 and issued on Oct. 28, 2003 as U.S. Pat. No. 6,638,747, which is a divisional of U.S. application Ser. No. 09/801,052, filed on Mar. 8, 2001 and issued on Apr. 9, 2002 as U.S. Pat. No. 6,368,842, which claims priority to U.S. Provisional Application No. 60/255,386, filed on Dec. 15, 2000.

FIELD OF THE INVENTION

The present invention is in the field of phospholipase proteins that are related to the phospholipase D subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Phospholipases

There are three major families of known human phospholipase enzymes: Phospholipase A2, Phospholipase C, and Phospholipase D.

Enzymes in the Phospholipase A2 family ("P1A2") hydrolyze the sn-2 fatty acid acyl ester bond of phosphoglycerides, releasing free fatty acids and lysophospholipids. The P1A2s constitute a diverse family of enzymes with respect to sequence, function, localization and divalent cation requirements. They play an important role in a variety of cellular processes, including the digestion and metabolism of phospholipids as well as the production of precursors for inflammatory reactions. The P1A2s have been classified into at least 5 groups (although different classification schemes exist and up to 10 groups have been identified by some authorities) based on their size, structure and need for divalent cations. Groups I, II and III all contain secreted forms of P1A, which are extracellular enzymes that have a low molecular mass and require calcium ions for catalysis. Groups IV and V contain cytosolic forms of P1A2s that have a high molecular mass and do not necessarily require calcium ions.

Amongst the best characterized of the P1A2 phospholipases are digestive enzymes secreted as zymogens by the pancreas. These enzymes, which are involved in the hydrolysis of dietary phospholipids, have strong homology to the venom phospholipases of snakes. Other P1A2s play important roles in the control of signaling cascades such as the cytosolic P1A2, Group IVA enzyme ("PLA2G4A") which catalyzes the release of arachidonic acid from membrane phospholipids. Arachidonic acid serves as a precursor for a wide spectrum of biological effectors, collectively known as eicosanoids (and including the prostaglandin group of molecules) that are involved in hemodynamic regulation, inflammatory responses and other cellular processes.

Another biologically active phospholipid, platelet-activating factor ("PAF") is hydrolyzed to metabolically-inactive degradation products by the group VII P1A2 known as PAF acetylhydrolase. Deficiency of PAF acetylhydrolase has been reported in patients with systemic lupus erythematosis and increased levels of PAF have been reported in children with acute asthmatic attacks. Elevated levels of the group II P1A2 known as PLA2G2A have been reported in plasma and synovial fluid in patients with inflammatory arthritis. Studies of a mouse colon cancer model showed that alleles of the murine ortholog of this gene were able to modify the number of tumors that developed in animals with multiple intestinal neoplasia (a mouse model of the human disorder known as familial adenomtous polyposis). Subsequent studies in humans showed mutations in PLA2G2A were associated with the risk of developing colorectal cancer. PLA2G2A is presumed to act through altering cellular microenvironments within the intestinal crypts of the colonic mucosa, although the precise mechanism by which this effect is exerted is not clear.

Enzymes in the Phospholipase C ("PLC") family catalyze the hydrolysis of the plasma membrane phospholipids, phosphatidyl inositol phosphate ("PIP") or phosphatidylinositol 4,5-biphosphate ("PIP2"), generating as products the second messengers, 1,4,5-inositol triphosphate ("IP3") and 1,2-diacylglycerol ("DAG"). Molecules belonging to the PLC gene family are divided into subfamilies, PLC-beta, PLC-gamma and PLC-delta. PLC-delta is distinguished from PLC-gamma by lack of the SH2 and SH3 domains that are essential for activation of PLC-gamma by tyrosine protein kinases. PLC-delta is distinguished from PLC-beta by lack of the C-terminal region of PLC-beta that is responsible for binding and activation of G proteins. Various PLC enzymes play important roles in signal transduction cascades throughout the body. Activating signals include hormones, growth factors and neurotransmitters. One of the functions of IP2 is to modulate intracellular calcium levels while DAG is involved in the activation of certain protein kinases and can promote membrane fusion in processes involving vesicular trafficking.

Enzymes in the Phospholipase D ("PLD") family catalyze the hydrolysis of phosphatidylcholine ("PC") and other phospholipids to produce phosphatidic acid. A range of agonists acting through G protein-coupled receptors and receptor tyrosine kinases stimulate this hydrolysis. Phosphatidic acid appears to be important as a second messenger capable of activating a diverse range of signaling pathways. PC-specific PLD activity has been implicated in numerous cellular pathways, including signal transduction, membrane trafficking, the regulation of mitosis, regulated secretion, cytoskeletal reorganization, transcriptional regulation and cell-cycle control. Many proteins are attached to the plasma membrane via a glysylphosphatidylinositol ("GPI") anchor. Phosphatidylinositol-glycan ("PIG")-specific PLDs selectively hydrolyze the inositol phosphate linkage, allowing release of the protein.

Phospholipase D

The protein provided by the present invention is a novel human phospholipase splice form that is related to the phospholipase D (PLD) family. In particular, the novel phospholipase splice form provided by the present invention lacks exon 2 found in a prior art phospholipase protein (patent seq W57899). PLD proteins are known to exist as alternative splice forms. For example, alternate splice variants of two PLD isoforms, termed PLD 1 and PLD2, have previously been identified (Steed et al., *FASEB J.* 1998 October;12(13):1309–17).

The phospholipase D family is characterized by a conserved HXKXXXXD motif and this characteristic motif is essential for the catalytic function of PLD. A subclass of PLD exists that is characterized by a second HXKXXXXD motif with a conserved Asp to Glu substitution. PLD enzymes play important roles in signal transduction and membrane vesicular trafficking in mammalian cells (Pedersen et al., *J Biol Chem* 1998 Nov. 20;273(47) :31494–504). In particular, PLD cleaves phosphatidylcholine in response to cell stimuli, thereby releasing phosphatidic acid, which is involved in numerous cellular responses that may play a role in, for example, regulation of secretion, mitogenesis, or cytoskeletal changes (Steed et al., *FASEB J.* 1998 October;12(13):1309–17).

The activity and regulation of recombinant human PLD2 are identical to that of recombinant mouse PLD2. Analysis of the amino acid sequences of the human PLD1 and PLD2 isoforms revealed Pleckstrin homology domains. (Steed et al., *FASEB J.* 1998 October;12(13):1309–17). Orthologs of PLD may exist in vaccinia virus (Pedersen et al., *J Biol Chem* 1998 Nov. 20;273(47):31494–504).

A murine PLD gene, termed sam-9 gene, has been found to be expressed at high levels in the brain, particularly in mature neurons of the forebrain, and the gene is turned on during late stages of neurogenesis (Pedersen et al., *J Biol Chem* 1998 Nov. 20;273(47):31494–504).

Phospholipase proteins, particularly members of the phospholipase D subfamily, are a major target for drug action and development. Accordingly, it is valuable to the field of pharmaceutical development to identify and characterize previously unknown members of this subfamily of phospholipase proteins. The present invention advances the state of the art by providing previously unidentified human phospholipase proteins that have homology to members of the phospholipase D subfamily.

SUMMARY OF THE INVENTION

The present invention is based in part on the identification of amino acid sequences of human phospholipase peptides and proteins that are related to the phospholipase D subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate phospholipase activity in cells and tissues that express the phospholipase. Experimental data as provided in FIG. 1 indicates expression in humans in the brain (including neuroblastomas and infant brain), uterus, lung, ovary adenocarcinomas, and leukocytes.

DESCRIPTION OF THE FIGURE SHEETS

FIG. 1 provides the nucleotide sequence of a cDNA molecule or transcript sequence that encodes the phospholipase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in the brain (including neuroblastomas and infant brain), uterus, lung, ovary adenocarcinomas, and leukocytes.

FIG. 2 provides the predicted amino acid sequence of the phospholipase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the phospholipase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at nine different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a phospholipase protein or part of a phospholipase protein and are related to the phospholipase D subfamily. Utilizing these sequences, additional genomic sequences were assembled and transcript and/or cDNA sequences were isolated and characterized. Based on this analysis, the present invention provides amino acid sequences of human phospholipase peptides and proteins that are related to the phospholipase D subfamily, nucleic acid sequences in the form of transcript sequences, cDNA sequences and/or genomic sequences that encode these phospholipase peptides and proteins, nucleic acid variation (allelic information), tissue distribution of expression, and information about the closest art known protein/peptide/domain that has structural or sequence homology to the phospholipase of the present invention.

In addition to being previously unknown, the peptides that are provided in the present invention are selected based on their ability to be used for the development of commercially important products and services. Specifically, the present peptides are selected based on homology and/or structural relatedness to known phospholipase proteins of the phospholipase D subfamily and the expression pattern observed. Experimental data as provided in FIG. 1 indicates expression in humans in the brain (including neuroblastomas and infant brain), uterus, lung, ovary adenocarcinomas, and leukocytes. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known phospholipase D family or subfamily of phospholipase proteins.

Specific Embodiments

Peptide Molecules

The present invention provides nucleic acid sequences that encode protein molecules that have been identified as being members of the phospholipase family of proteins and are related to the phospholipase D subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the phospholipase peptides of the present invention, phospholipase peptides, or peptides/proteins of the present invention.

The present invention provides isolated peptide and protein molecules that consist of, consist essentially of, or comprise the amino acid sequences of the phospholipase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the phospholipase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated phospholipase peptide can be purified from cells that naturally express it, purified from cells that have been altered to express it (recombinant), or synthesized using known protein synthesis methods. Experimental data as provided in FIG. 1 indicates expression in humans in the brain (including neuroblastomas and infant brain), uterus, lung, ovary adenocarcinomas, and leukocytes. For example, a nucleic acid molecule encoding the phospholipase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the phospholipase peptides of the present invention are the naturally occurring mature proteins. A brief description of how various types of these proteins can be made/isolated is provided below.

The phospholipase peptides of the present invention can be attached to heterologous sequences to form chimeric or fusion proteins. Such chimeric and fusion proteins comprise a phospholipase peptide operatively linked to a heterologous protein having an amino acid sequence not substantially homologous to the phospholipase peptide. "Operatively linked" indicates that the phospholipase peptide and the heterologous protein are fused in-frame. The heterologous protein can be fused to the N-terminus or C-terminus of the phospholipase peptide.

In some uses, the fusion protein does not affect the activity of the phospholipase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant phospholipase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A phospholipase peptide-encoding nucleic acid can be cloned into such an expression vector such that the fusion moiety is linked in-frame to the phospholipase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the phospholipase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the phospholipase peptides of the present invention as well as being encoded by the same genetic locus as the phospholipase peptide provided herein. The gene encoding the novel phospholipase protein of the present invention is located on a genome component that has been mapped to human chromosome 2 (as indicated in FIG. 3), which is supported by multiple lines of evidence, such as STS and BAC map data.

Allelic variants of a phospholipase peptide can readily be identified as being a human protein having a high degree (significant) of sequence homology/identity to at least a portion of the phospholipase peptide as well as being encoded by the same genetic locus as the phospholipase peptide provided herein. Genetic locus can readily be determined based on the genomic information provided in FIG. 3, such as the genomic sequence mapped to the reference human. The gene encoding the novel phospholipase protein of the present invention is located on a genome component that has been mapped to human chromosome 2 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a phospholipase peptide encoding nucleic acid molecule under stringent conditions as more fully described below.

FIG. 3 provides information on SNPs that have been found in the gene encoding the phospholipase proteins of the present invention. SNPs were identified at nine different nucleotide positions. SNPs outside the ORF and in introns may affect control/regulatory elements.

Paralogs of a phospholipase peptide can readily be identified as having some degree of significant sequence homology/identity to at least a portion of the phospholipase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a phospholipase peptide encoding nucleic acid molecule under moderate to stringent conditions as more fully described below.

Orthologs of a phospholipase peptide can readily be identified as having some degree of significant sequence homology/identity to at least a portion of the phospholipase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a phospholipase peptide encoding nucleic acid molecule under moderate to stringent conditions, as more fully described below, depending on the degree of relatedness of the two organisms yielding the proteins.

Non-naturally occurring variants of the phospholipase peptides of the present invention can readily be generated using recombinant techniques. Such variants include, but are not limited to deletions, additions and substitutions in the amino acid sequence of the phospholipase peptide. For example, one class of substitutions are conserved amino acid substitution. Such substitutions are those that substitute a given amino acid in a phospholipase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant phospholipase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as phospholipase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the phospholipase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a phospholipase peptide. Such fragments can be chosen based on the ability to retain one or more of the biological activities of the phospholipase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the phospholipase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in phospholipase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the phospholipase peptides of the present invention also encompass derivatives or analogs in which a substituted amino acid residue is not one encoded by the genetic code, in which a substituent group is included, in which the mature phospholipase peptide is fused with another compound, such as a compound to increase the half-life of the phospholipase peptide (for example, polyethylene glycol), or in which the additional amino acids are fused to the mature phospholipase peptide, such as a leader or secretory sequence or a sequence for purification of the mature phospholipase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed disease state). Where the protein binds or potentially binds to another protein or ligand (such as, for example, in a phospholipase-effector protein interaction or phospholipase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, phospholipases isolated from humans and their human/mammalian orthologs serve as targets for identifying agents for use in mammalian therapeutic applications, e.g. a human drug, particularly in modulating a biological or pathological response in a cell or tissue that expresses the phospholipase. Experimental data as provided in FIG. 1 indicates that phospholipase proteins of the present invention are expressed in humans in the brain (including neuroblastomas and infant brain), uterus, lung, ovary adenocarcinomas, and leukocytes. Specifically, a virtual northern blot shows expression in the brain (including neuroblastomas and infant brain), uterus, lung, and ovary adenocarcinomas. In addition, PCR-based tissue screening panels indicate expression in leukocytes. A large percentage of pharmaceutical agents are being developed that modulate the activity of phospholipase proteins, particularly members of the phospholipase D subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the brain (including neuroblastomas and infant brain), uterus, lung, ovary adenocarcinomas, and leukocytes. Such uses can readily be determined using the information provided herein, that which is known in the art, and routine experimentation.

The proteins of the present invention (including variants and fragments that may have been disclosed prior to the present invention) are useful for biological assays related to phospholipases that are related to members of the phospholipase D subfamily. Such assays involve any of the known phospholipase functions or activities or properties useful for diagnosis and treatment of phospholipase-related conditions that are specific for the subfamily of phospholipases that the one of the present invention belongs to, particularly in cells and tissues that express the phospholipase. Experimental data as provided in FIG. 1 indicates that phospholipase proteins of the present invention are expressed in humans in the brain (including neuroblastomas and infant brain), uterus, lung, ovary adenocarcinomas, and leukocytes. Specifically, a virtual northern blot shows expression in the brain (including neuroblastomas and infant brain), uterus, lung, and ovary adenocarcinomas. In addition, PCR-based tissue screening panels indicate expression in leukocytes.

The proteins of the present invention are also useful in drug screening assays, in cell-based or cell-free systems. Cell-based systems can be native, i.e., cells that normally express the phospholipase, as a biopsy or expanded in cell culture. Experimental data as provided in FIG. 1 indicates expression in humans in the brain (including neuroblastomas and infant brain), uterus, lung, ovary adenocarcinomas, and leukocytes. In an alternate embodiment, cell-based assays involve recombinant host cells expressing the phospholipase protein.

The polypeptides can be used to identify compounds that modulate phospholipase activity of the protein in its natural state or an altered form that causes a specific disease or pathology associated with the phospholipase. Both the phospholipases of the present invention and appropriate variants and fragments can be used in high-throughput screens to assay candidate compounds for the ability to bind to the phospholipase. These compounds can be further screened against a functional phospholipase to determine the effect of the compound on the phospholipase activity. Further, these compounds can be tested in animal or invertebrate systems to determine activity/effectiveness. Compounds can be identified that activate (agonist) or inactivate (antagonist) the phospholipase to a desired degree.

Further, the proteins of the present invention can be used to screen a compound for the ability to stimulate or inhibit interaction between the phospholipase protein and a molecule that normally interacts with the phospholipase protein, e.g. a substrate or a component of the signal pathway that the phospholipase protein normally interacts (for example, another phospholipase). Such assays typically include the steps of combining the phospholipase protein with a candidate compound under conditions that allow the phospholipase protein, or fragment, to interact with the target molecule, and to detect the formation of a complex between the protein and the target or to detect the biochemical consequence of the interaction with the phospholipase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')₂, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant phospholipases or appropriate fragments containing mutations that affect phospholipase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) phospholipase activity. The assays typically involve an assay of events in the signal transduction pathway that indicate phospholipase activity. Thus, the phosphorylation of a substrate, activation of a protein, a change in the expression of genes that are up- or down-regulated in response to the phospholipase protein dependent signal cascade can be assayed.

Any of the biological or biochemical functions mediated by the phospholipase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the phospholipase can be assayed. Experimental data as provided in FIG. 1 indicates that phospholipase proteins of the present invention are expressed in humans in the brain (including neuroblastomas and infant brain), uterus, lung, ovary adenocarcinomas, and leukocytes. Specifically, a virtual northern blot shows expression in the brain (including neuroblastomas and infant brain), uterus, lung, and ovary adenocarcinomas. In addition, PCR-based tissue screening panels indicate expression in leukocytes.

Binding and/or activating compounds can also be screened by using chimeric phospholipase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native phospholipase. Accordingly, a different set of signal transduction components is available as an end-point assay for activation. This allows for assays to be performed in other than the specific host cell from which the phospholipase is derived.

The proteins of the present invention are also useful in competition binding assays in methods designed to discover compounds that interact with the phospholipase (e.g. binding partners and/or ligands). Thus, a compound is exposed to a phospholipase polypeptide under conditions that allow the compound to bind or to otherwise interact with the polypeptide. Soluble phospholipase polypeptide is also added to the mixture. If the test compound interacts with the soluble phospholipase polypeptide, it decreases the amount of complex formed or activity from the phospholipase target. This type of assay is particularly useful in cases in which compounds are sought that interact with specific regions of the phospholipase. Thus, the soluble polypeptide that competes with the target phospholipase region is designed to contain peptide sequences corresponding to the region of interest.

To perform cell free drug screening assays, it is sometimes desirable to immobilize either the phospholipase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of phospholipase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phospholipase-binding protein and a candidate compound are incubated in the phospholipase protein-presenting wells and the amount of complex trapped in the well can be quantitated. Methods for detecting such complexes, in addition to those described above for the GST-immobilized complexes, include immunodetection of complexes using antibodies reactive with the phospholipase protein target molecule, or which are reactive with phospholipase protein and compete with the target molecule, as well as enzyme-linked assays which rely on detecting an enzymatic activity associated with the target molecule.

Agents that modulate one of the phospholipases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of phospholipase protein activity identified according to these drug screening assays can be used to treat a subject with a disorder mediated by the phospholipase pathway, by treating cells or tissues that express the phospholipase. Experimental data as provided in FIG. 1 indicates expression in humans in the brain (including neuroblastomas and infant brain), uterus, lung, ovary adenocarcinomas, and leukocytes. These methods of treatment include the steps of administering a modulator of phospholipase activity in a pharmaceutical composition to a subject in need of such treatment, the modulator being identified as described herein.

In yet another aspect of the invention, the phospholipase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the phospholipase and are involved in phospholipase activity. Such phospholipase-binding proteins are also likely to be involved in the propagation of signals by the phospholipase proteins or phospholipase targets as, for example, downstream elements of a phospholipase-mediated signaling pathway. Alternatively, such phospholipase-binding proteins are likely to be phospholipase inhibitors.

The two-hybrid system is based on the modular nature of most transcription factors, which consist of separable DNA-binding and activation domains. Briefly, the assay utilizes two different DNA constructs. In one construct, the gene that codes for a phospholipase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a phospholipase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the phospholipase protein.

This invention further pertains to novel agents identified by the above-described screening assays. Accordingly, it is within the scope of this invention to further use an agent identified as described herein in an appropriate animal model. For example, an agent identified as described herein (e.g., a phospholipase-modulating agent, an antisense phospholipase nucleic acid molecule, a phospholipase-specific antibody, or a phospholipase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The phospholipase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the brain (including neuroblastomas and infant brain), uterus, lung, ovary adenocarcinomas, and leukocytes. The method involves contacting a biological sample with a compound capable of interacting with the phospholipase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered phospholipase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phospholipase protein in which one or more of the phospholipase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and phospholipase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the brain (including neuroblastomas and infant brain), uterus, lung, ovary adenocarcinomas, and leukocytes. Accordingly, methods for treatment include the use of the phospholipase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the phospholipase proteins. Antibodies can be prepared from any region of the peptide as described herein. However, preferred regions will include those involved in function/activity and/or phospholipase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that phospholipase proteins of the present invention are expressed in humans in the brain (including neuroblastomas and infant brain), uterus, lung, ovary adenocarcinomas, and leukocytes. Specifically, a virtual northern blot shows expression in the brain (including neuroblastomas and infant brain), uterus, lung, and ovary adenocarcinomas. In addition, PCR-based tissue screening panels indicate expression in leukocytes. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the brain (including neuroblastomas and infant brain), uterus, lung, ovary adenocarcinomas, and leukocytes. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the brain (including neuroblastomas and infant brain), uterus, lung, ovary adenocarcinomas, and leukocytes. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the brain (including neuroblastomas and infant brain), uterus, lung, ovary adenocarcinomas, and leukocytes. Thus, where a specific protein has been correlated with expression in a specific tissue, antibodies that are specific for this protein can be used to identify a tissue type.

The antibodies are also useful for inhibiting protein function, for example, blocking the binding of the phospholipase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a phospholipase peptide or protein of the present invention (cDNA, transcript and genomic sequence). Such nucleic acid molecules will consist of, consist essentially of, or comprise a nucleotide sequence that encodes one of the phospholipase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the phospholipase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the phospholipase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel phospholipase protein of the present invention is located on a genome component that has been mapped to human chromosome 2 (as indicated in FIG. 3), which is supported by multiple lines of evidence, such as STS and BAC map data.

FIG. 3 provides information on SNPs that have been found in the gene encoding the phospholipase proteins of the present invention. SNPs were identified at nine different nucleotide positions. SNPs outside the ORF and in introns may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45 C, followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate fill-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at nine different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel phospholipase protein of the present invention is located on a genome component that has been mapped to human chromosome 2 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that phospholipase proteins of the present invention are expressed in humans in the brain (including neuroblastomas and infant brain), uterus, lung, ovary adenocarcinomas, and leukocytes. Specifically, a virtual northern blot shows expression in the brain (including neuroblastomas and infant brain), uterus, lung, and ovary adenocarcinomas. In addition, PCR-based tissue screening panels indicate expression in leukocytes. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in phospholipase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a phospholipase protein, such as by measuring a level of a phospholipase-encoding nucleic acid in a sample of cells from a subject e.g., mRNA or genomic DNA, or determining if a phospholipase gene has been mutated. Experimental data as provided in FIG. 1 indicates that phospholipase proteins of the present invention are expressed in humans in the brain (including neuroblastomas and infant brain), uterus, lung, ovary adenocarcinomas, and leukocytes. Specifically, a virtual northern blot shows expression in the brain (including neuroblastomas and infant brain), uterus, lung, and ovary adenocarcinomas. In addition, PCR-based tissue screening panels indicate expression in leukocytes.

Nucleic acid expression assays are useful for drug screening to identify compounds that modulate phospholipase nucleic acid expression.

The invention thus provides a method for identifying a compound that can be used to treat a disorder associated with nucleic acid expression of the phospholipase gene, particularly biological and pathological processes that are mediated by the phospholipase in cells and tissues that express it. Experimental data as provided in FIG. 1 indicates expression in humans in the brain (including neuroblastomas and infant brain), uterus, lung, ovary adenocarcinomas, and leukocytes. The method typically includes assaying the ability of the compound to modulate the expression of the phospholipase nucleic acid and thus identifying a compound that can be used to treat a disorder characterized by undesired phospholipase nucleic acid expression. The assays can be performed in cell-based and cell-free systems. Cell-based assays include cells naturally expressing the phospholipase nucleic acid or recombinant cells genetically engineered to express specific nucleic acid sequences.

The assay for phospholipase nucleic acid expression can involve direct assay of nucleic acid levels, such as mRNA levels, or on collateral compounds involved in the signal pathway. Further, the expression of genes that are up- or down-regulated in response to the phospholipase protein signal pathway can also be assayed. In this embodiment the regulatory regions of these genes can be operably linked to a reporter gene such as luciferase.

Thus, modulators of phospholipase gene expression can be identified in a method wherein a cell is contacted with a candidate compound and the expression of mRNA determined. The level of expression of phospholipase mRNA in the presence of the candidate compound is compared to the level of expression of phospholipase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate phospholipase nucleic acid expression in cells and tissues that express the phospholipase. Experimental data as provided in FIG. 1 indicates that phospholipase proteins of the present invention are expressed in humans in the brain (including neuroblastomas and infant brain), uterus, lung, ovary adenocarcinomas, and leukocytes. Specifically, a virtual northern blot shows expression in the brain (including neuroblastomas and infant brain), uterus, lung, and ovary adenocarcinomas. In addition, PCR-based tissue screening panels indicate expression in leukocytes. Modulation includes both up-regulation (i.e. activation or agonization) or down-regulation (suppression or antagonization) or nucleic acid expression.

Alternatively, a modulator for phospholipase nucleic acid expression can be a small molecule or drug identified using the screening assays described herein as long as the drug or small molecule inhibits the phospholipase nucleic acid expression in the cells and tissues that express the protein. Experimental data as provided in FIG. 1 indicates expression in humans in the brain (including neuroblastomas and infant brain), uterus, lung, ovary adenocarcinomas, and leukocytes.

The nucleic acid molecules are also useful for monitoring the effectiveness of modulating compounds on the expression or activity of the phospholipase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in phospholipase nucleic acid expression, and particularly in qualitative changes that lead to pathology. The nucleic acid molecules can be used to detect mutations in phospholipase genes and gene expression products such as mRNA. The nucleic acid molecules can be used as hybridization probes to detect naturally occurring genetic mutations in the phospholipase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phospholipase gene associated with a dysfunction provides a diagnostic tool for an active disease or susceptibility to disease when the disease results from overexpression, underexpression, or altered expression of a phospholipase protein.

Individuals carrying mutations in the phospholipase gene can be detected at the nucleic acid level by a variety of techniques. FIG. 3 provides information on SNPs that have been found in the gene encoding the phospholipase proteins of the present invention. SNPs were identified at nine different nucleotide positions. SNPs outside the ORF and in introns may affect control/regulatory elements. The gene encoding the novel phospholipase protein of the present invention is located on a genome component that has been mapped to human chromosome 2 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91:360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a phospholipase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant phospholipase gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al, Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the phospholipase gene in an individual in order to select an appropriate compound or dosage regimen for treatment. FIG. 3 provides information on SNPs that have been found in the gene encoding the phospholipase proteins of the present invention. SNPs were identified at nine different nucleotide positions. SNPs outside the ORF and in introns may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control phospholipase gene expression in cells, tissues, and organisms. A DNA antisense nucleic acid molecule is designed to be complementary to a region of the gene involved in transcription, preventing transcription and hence production of phospholipase protein. An antisense RNA or DNA nucleic acid molecule would hybridize to the mRNA and thus block translation of mRNA into phospholipase protein.

Alternatively, a class of antisense molecules can be used to inactivate mRNA in order to decrease expression of phospholipase nucleic acid. Accordingly, these molecules can treat a disorder characterized by abnormal or undesired phospholipase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the phospholipase protein, such as substrate binding.

The nucleic acid molecules also provide vectors for gene therapy in patients containing cells that are aberrant in phospholipase gene expression. Thus, recombinant cells, which include the patient's cells that have been engineered ex vivo and returned to the patient, are introduced into an individual where the cells produce the desired phospholipase protein to treat the individual.

The invention also encompasses kits for detecting the presence of a phospholipase nucleic acid in a biological sample. Experimental data as provided in FIG. 1 indicates that phospholipase proteins of the present invention are expressed in humans in the brain (including neuroblastomas and infant brain), uterus, lung, ovary adenocarcinomas, and leukocytes. Specifically, a virtual northern blot shows expression in the brain (including neuroblastomas and infant brain), uterus, lung, and ovary adenocarcinomas. In addition, PCR-based tissue screening panels indicate expression in leukocytes. For example, the kit can comprise reagents such as a labeled or labelable nucleic acid or agent capable of detecting phospholipase nucleic acid in a biological sample; means for determining the amount of phospholipase nucleic acid in the sample; and means for comparing the amount of phospholipase nucleic acid in the sample with a standard. The compound or agent can be packaged in a suitable container. The kit can further comprise instructions for using the kit to detect phospholipase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the phospholipase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the phospholipase gene of the present invention. FIG. 3 provides information on SNPs that have been found in the gene encoding the phospholipase proteins of the present invention. SNPs were identified at nine different nucleotide positions. SNPs outside the ORF and in introns may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified phospholipase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli,* Streptomyces, and *Salmonella typhimurium.* Eukaryotic cells include, but are not limited to, yeast, insect cells such as *Drosophila,* animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterophospholipase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al, *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as phospholipases, appropriate secretion signals are incorporated into the vector. The signal sequence can be endogenous to the peptides or heterologous to these peptides.

Where the peptide is not secreted into the medium, which is typically the case with phospholipases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a phospholipase protein or peptide that can be further purified to produce desired amounts of phospholipase protein or fragments. Thus, host cells containing expression vectors are useful for peptide production.

Host cells are also useful for conducting cell-based assays involving the phospholipase protein or phospholipase protein fragments, such as those described above as well as other formats known in the art. Thus, a recombinant host cell expressing a native phospholipase protein is useful for assaying compounds that stimulate or inhibit phospholipase protein function.

Host cells are also useful for identifying phospholipase protein mutants in which these functions are affected. If the mutants naturally occur and give rise to a pathology, host cells containing the mutations are useful to assay compounds that have a desired effect on the mutant phospholipase protein (for example, stimulating or inhibiting function) which may not be indicated by their effect on the native phospholipase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a phospholipase protein and identifying and evaluating modulators of phospholipase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the phospholipase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the phospholipase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, phospholipase protein activation, and signal transduction, may not be evident from in vitro cell-free or cell-based assays. Accordingly, it is useful to provide non-human transgenic animals to assay in vivo phospholipase protein function, including substrate interaction, the effect of specific mutant phospholipase proteins on phospholipase protein function and substrate interaction, and the effect of chimeric phospholipase proteins. It is also possible to assess the effect of null mutations, that is, mutations that substantially or completely eliminate one or more phospholipase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. An isolated nucleic acid molecule encoding a phospholipase D protein, said isolated nucleic acid molecule comprising a nucleotide sequence selected from the group consisting of:
   (a) a nucleotide sequence that encodes a protein comprising amino acid sequence of SEQ ID NO:2;
   (b) a nucicotide sequence comprising the nucleic acid sequence of SEQ ID NO: 1;
   (c) a nucleotide sequence comprising the nucleic acid sequence of SEQ ID NO: 3; and
   (d) a nucleotide sequence that is completely complementary to a nucleotide sequence of (a)–(c).

2. A nucleic acid vector comprising the nucleic acid molecule of claim 1.

3. A recombinant host cell containing the vector of claim 2.

4. A process for producing a polypeptide having phospholipase activity comprising culturing the host cell of claim 3 under conditions sufficient for the production of said polypeptide, and recovering the polypeptide from the host cell culture.

5. An isolated polynucleotide comprising a nucleotide sequence set forth in SEQ ID NO:1.

6. An isolated polynucleotide comprising a nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO:2 may be expressed by a cell transformed with said vector.

9. A vector according to claim 8, wherein said isolated nucleic acid molecule is operatively linked to a promoter sequence.

10. An isolated nucleic acid molecule consisting of a nucleotide sequence that is completely complementary to a nucleotide sequence of claim 1.

11. An isolated nucleic acid molecule encoding protein having phospholipase activity, said nucleic acid molecule sharing at least 99% percent homology with a nucleic acid molecule shown in SEQ ID NOS:1 or 3.

* * * * *

SEQUENCE LISTING

<160> NUMBER OF SEQ ID NOS: 5

<210> SEQ ID NO 1
<211> LENGTH: 1872
<212> TYPE: DNA
<213> ORGANISM: Homo sapiens

<400> SEQUENCE: 1

```
gaccctgaca cacccacctt ctcacctggg ctctgcgtat cccccagcct tgagggaaga      60
tgaagcctaa actgatgtac caggagaaag cccgctgggt cctgctggtc ctcattctgg     120
cggttgtggg cttcggagcc ctgatgactc agctgtttct atgggaatac ggcgacttgc     180
atctctttgg gcccaaccag cgcccagccc cctgctatga cccttgcgaa gcagtgctgg     240
tggaaagcat tcctgagggc ctggacttcc ccaatgcctc cacggggaac ccttccacca     300
gccaggcctg gctgggcctg ctcgccggtg cgcacgcag cctggacatc gcctccttct      360
actggaccct caccaacaat gacacccaca cgcaggagcc ctctgcccag cagggtgagg     420
aggtcctccg gcagctgcag accctggcac caaagggcgt gaacgtccgc atcgctgtga     480
gcaagcccag cgggcccag ccacaggcgg acctgcaggc tctgctgcag agcggtgccc      540
aggtccgcat ggtggacatg cagaagctga cccatggcgt cctgcatacc aagttctggg     600
tggtggacca gacccacttc tacctgggca gtgccaacat ggactggcgt tcactgaccc     660
aggtcaagga gctgggcgtg gtcatgtaca actgcagctg cctggctcga gacctgacca     720
```

-continued

```
agatctttga ggcctactgg ttcctgggcc aggcaggcag ctccatccca tcaacttggc    780
cccggttcta tgacacccgc tacaaccaag agacaccaat ggagatctgc ctcaatggaa    840
cccctgctct ggcctacctg gcgagtgcgc ccccaccct  gtgtccaagt ggccgcactc    900
cagacctgaa ggctctactc aacgtggtgg acaatgcccg gagtttcatc tacgtcgctg    960
tcatgaacta cctgcccact ctggagttct cccaccctca caggttctgg cctgccattg   1020
acgatgggct gcggcgggcc acctacgagc gtggcgtcaa ggtgcgcctg ctcatcagct   1080
gctggggaca ctcggagcca tccatgcggg ccttcctgct ctctctggct gccctgcgtg   1140
acaaccatac ccactctgac atccaggtga aactctttgt ggtccccgcg gatgaggccc   1200
aggctcgaat cccatatgcc cgtgtcaacc acaacaagta catggtgact gaacgcgcca   1260
cctacatcgg aacctccaac tggtctggca actacttcac ggagacggcg ggcacctcgc   1320
tgctggtgac gcagaatggg aggggcggcc tgcggagcca gctggaggcc atttcctga   1380
gggactggga ctccccttac agccatgacc ttgacacctc agctgacagc gtgggcaacg   1440
cctgccgcct gctctgaggc ccgatccagt gggcaggcca aggcctgctg gcccccgcg   1500
gacccaggtg ctctgggtca cggtcccctgt ccccgcaccc ccgcttctgt ctgccccatt  1560
gtggctcctc aggctctctc ccctgctctc ccacctctac ctccaccccc accgggcctg   1620
acgctgtggc cccgggaccc agcagagctg ggggagggat cagcccccaa agaaatgggg   1680
gtgcatgctg ggcctggccc cctggcccac cccacttttc cagggcaaaa agggcccagg   1740
gttataataa gtaaataact tgtctgtaaa aaaaaaaaa aaaaaaaaaa aaaaaaaaa     1800
aaaaaaaaaa aaaaaaaaaa aaaaaaaaaa aaaaaaaaaa aaaaaaaaaa aaaaaaaaaa   1860
aaaaaaaaaa aa                                                       1872
```

<210> SEQ ID NO 2
<211> LENGTH: 465
<212> TYPE: PRT
<213> ORGANISM: Homo sapiens

<400> SEQUENCE: 2

```
Met Lys Pro Lys Leu Met Tyr Gln Glu Lys Ala Arg Trp Val Leu Leu
 1               5                  10                  15

Val Leu Ile Leu Ala Val Val Gly Phe Gly Ala Leu Met Thr Gln Leu
             20                  25                  30

Phe Leu Trp Glu Tyr Gly Asp Leu His Leu Phe Gly Pro Asn Gln Arg
         35                  40                  45

Pro Ala Pro Cys Tyr Asp Pro Cys Glu Ala Val Leu Val Glu Ser Ile
     50                  55                  60

Pro Glu Gly Leu Asp Phe Pro Asn Ala Ser Thr Gly Asn Pro Ser Thr
 65                  70                  75                  80

Ser Gln Ala Trp Leu Gly Leu Leu Ala Gly Ala His Ser Ser Leu Asp
                 85                  90                  95

Ile Ala Ser Phe Tyr Trp Thr Leu Thr Asn Asn Asp Thr His Thr Gln
            100                 105                 110

Glu Pro Ser Ala Gln Gln Gly Glu Glu Val Leu Arg Gln Leu Gln Thr
        115                 120                 125

Leu Ala Pro Lys Gly Val Asn Val Arg Ile Ala Val Ser Lys Pro Ser
    130                 135                 140

Gly Pro Gln Pro Gln Ala Asp Leu Gln Ala Leu Leu Gln Ser Gly Ala
145                 150                 155                 160

Gln Val Arg Met Val Asp Met Gln Lys Leu Thr His Gly Val Leu His
```

```
              165                 170                 175
Thr Lys Phe Trp Val Val Asp Gln Thr His Phe Tyr Leu Gly Ser Ala
            180                 185                 190
Asn Met Asp Trp Arg Ser Leu Thr Gln Val Lys Glu Leu Gly Val Val
            195                 200                 205
Met Tyr Asn Cys Ser Cys Leu Ala Arg Asp Leu Thr Lys Ile Phe Glu
            210                 215                 220
Ala Tyr Trp Phe Leu Gly Gln Ala Gly Ser Ser Ile Pro Ser Thr Trp
225                 230                 235                 240
Pro Arg Phe Tyr Asp Thr Arg Tyr Asn Gln Glu Thr Pro Met Glu Ile
                245                 250                 255
Cys Leu Asn Gly Thr Pro Ala Leu Ala Tyr Leu Ala Ser Ala Pro Pro
            260                 265                 270
Pro Leu Cys Pro Ser Gly Arg Thr Pro Asp Leu Lys Ala Leu Leu Asn
            275                 280                 285
Val Val Asp Asn Ala Arg Ser Phe Ile Tyr Val Ala Val Met Asn Tyr
            290                 295                 300
Leu Pro Thr Leu Glu Phe Ser His Pro His Arg Phe Trp Pro Ala Ile
305                 310                 315                 320
Asp Asp Gly Leu Arg Arg Ala Thr Tyr Glu Arg Gly Val Lys Val Arg
                325                 330                 335
Leu Leu Ile Ser Cys Trp Gly His Ser Glu Pro Ser Met Arg Ala Phe
            340                 345                 350
Leu Leu Ser Leu Ala Ala Leu Arg Asp Asn His Thr His Ser Asp Ile
            355                 360                 365
Gln Val Lys Leu Phe Val Val Pro Ala Asp Glu Ala Gln Ala Arg Ile
            370                 375                 380
Pro Tyr Ala Arg Val Asn His Asn Lys Tyr Met Val Thr Glu Arg Ala
385                 390                 395                 400
Thr Tyr Ile Gly Thr Ser Asn Trp Ser Gly Asn Tyr Phe Thr Glu Thr
                405                 410                 415
Ala Gly Thr Ser Leu Leu Val Thr Gln Asn Gly Arg Gly Gly Leu Arg
            420                 425                 430
Ser Gln Leu Glu Ala Ile Phe Leu Arg Asp Trp Asp Ser Pro Tyr Ser
            435                 440                 445
His Asp Leu Asp Thr Ser Ala Asp Ser Val Gly Asn Ala Cys Arg Leu
            450                 455                 460
Leu
465

<210> SEQ ID NO 3
<211> LENGTH: 16063
<212> TYPE: DNA
<213> ORGANISM: Homo sapiens

<400> SEQUENCE: 3
ggaggatcac ttgagtccag gagttcagcc tgggcaataa gcaagacccc gtctatacaa    60
aattaaaaaa aaaaaaatta gctgcggctg ggcgcggtgg ctcatgcctg taatcccagc   120
acttttgggg gcctagacgg gcggatcacg aggtcaggag atcgagacca tcctggctaa   180
cacggtgaaa ccccatctct actaaaaaat acaaaaaaaa aattagccgg gcatggtggc   240
gggcgcctgt agtcccagct actcgggaag ctgaggtggg cgaattgctc gaaccaggga   300
ggtggaggtt gcagtgagcc gagatggcgc cactgcactc cagcgtggga gagacagagc   360
```

-continued

```
gagactgcgt ctccaaaaaa aaaaaaaaaa gcagctgggc atggtggcac gtgcctgtag    420
tcccagctgc ttgggaggct gaggcaggag gattgcttga gcctgggaag ttgaggccgc    480
agtgagctat gatcatgctg ctgcactcca gcctagggaa cagaactctg cactaaaaaa    540
aagaaaagaa aagaaaagaa aataggctta caataaaaag caatcttgac ctaccccaaa    600
atcccactcc cttgaagaca accacttctg ccctgttgct tctctcagta atactccttt    660
tctgcagtta tctcttgact tcctgccatg tgtgtttggg ggagcttgag ggaagagggt    720
gtccctgtct cattgagaga ggtgccaccc tgccgtgaaa agaggtgcca ccctctgtca    780
attaggagag gagggatgag agaggaaagg ggtctccagt gtatttctcc agccggggcc    840
ttaaatccct cttgggagat atgggatggg gtggatcgga aaataaattt ttttaaatcc    900
ctaccaaaat atcagctggc tttttttaaa aaatcaaata ccaaaatcta aatagactcc    960
aacagaaaat tcaccatctc ctctgacctt tcttcccat  ctcatgctgt gaactgtctt   1020
ctgttgactt tatcgctacc tttcttcatt ctgttattca accatgatct ctccgtttca   1080
ttttataagc gttttattaa tttcatttat gtatttattt ttgactaggt aatgcatgtc   1140
catggtacac aaattcacaa ggtttgtaaa tgagaaaaga cgtgaggttc cttttgttct   1200
ttacctgtgg cctccctgcc ctacacgggg actctagggt ggaatgtagc aaagcccatc   1260
caccagccat gtactacccc caacccggc  caggctggag cgaccgtgtc tggggagccg   1320
agccccgctt ctcgctgcgg tgagcccgga ctggggcacg cactgcgcag actccccgct   1380
gcagtgggcg gagctcccac aggccccgcc ccctcctccc accctcgttc agcctgtcca   1440
gacagaagct ggggcccagc ggaggtagca gcagacgcct gagagcgagg ccgaggcccc   1500
tcaggggtag gtgggggggag gctggctggg gggatgggca gcggggtggc agggaggccc   1560
cgatgatccc tggctgagct gtgtggtgtg ggggcacctg agggcggagg agccacctag   1620 aatataccc  ctgtcccagg gctgagaaaa gccaggcaca aagacctggg gctccgctga   1680
cctcatccag cgctgccttt ctgggggtgt ctacaggttg gaggagggag aagggggctg   1740
ctagagggga gctgcgtggg tgctgatggg ggcagggtgg gcactgcaga gtgaagagca   1800
ggcagcagag cgttggattt tgagggattt cgaaatcctg ctgaccagtg accagcttcc   1860 tcttttggg  gtggtgggca gtgtgccagt ggccccatg  attatgaata gcccaagac    1920 taatcactct tctgtgatgt ctgtccctgg aaagcgtaga acaccccaca cagtgcccac   1980
ttttgttctg ccagtttgga gaccctgaca cacccacctt ctcacctggg ctctgcgtat   2040
cccccagcct tgagggaaga tgaagcctaa actgatgtac caggaggtag gtggattggg   2100
gggctcagca gggtggaact gggtacagtg ggggtggggg ttcccaagag ccacctgtca   2160
cccccgttgt tgtccccatc cccagctgaa ggtgcctgca gaggagcccg ccaatgagct   2220
gcccatgaat gagattgagg cgtggaaggc tgcggaaaag gtaggagccc tccgccaccc   2280
tcgctctgtc tcagagacag gctgggctgc ccccctcggg ctggctgacc acctcctcct   2340
ccccacagaa agcccgctgg gtcctgctgg tcctcattct ggcggttgtg ggcttcggag   2400
ccctgatgac tcagctgttt ctatgggaat acggcgactt gcatctcttt gggcccaacc   2460
agcgcccagc ccctgctat  gacccttgcg agtaagtggg gggtgctgca cttggtgggg   2520 gagggcctg  ccagaccagg tacacttaag cacacactaa acagggcctg cactcagccc   2580
tacccagcgc ttgcgacaag tgaggaggtt gcaggctccc aagtgctcgc ccgccccctc   2640
ctcctccaca cacatagttt ctatggcagc cacagcgtca tcttctgtca ggcctgtgaa   2700
cagacacagc atcttccacc cacatctgtg gacccacaca cacatctcaa tacacgacct   2760
```

-continued

```
tccttccaca cctctagaca gacacgcaga ggatcatgag tccaggcacg cattcaaata    2820
cacacagttt taaaaaattt tttttaaaag aaaagaaaaa ctcaaataca gtttagctgg    2880
gcttggtggc tcacgcctgt aattgcaaca ctttgcgggg ctgaggcggg aggattgctt    2940
gagcccagga gttccagacc agcctgggca atgtagtgcg gctccatctc tactaaaagt    3000
aaaaaaagta accaggcata ctggtgcaca cctgtagtcc cagctactca agaggttgag    3060
gcgggaggat cgcttgagcc caggggttcg aggctgcagt gagctgagat ggcgccactg    3120
cgcttccagc ctgggggaca gggcaagact ctgtctctaa aaaaaaaaaa atacagtcta    3180
tccaacacac ccatggacgg acagctgagc actcacctcc cagcccttgc tctccggcac    3240
cgtatggctg atagcatccc ccacccccca gagcagtgct ggtggaaagc attcctgagg    3300
gcctggactt ccccaatgcc tccacgggga acccttccac cagccaggcc tggctgggcc    3360
tgctcgccgg tgcgcacagc agcctggaca tcgcctcctt ctactggacc ctcaccaaca    3420
atgacaccca cacgcaggag ccctctgccc agcaggtacc tgcaaccttg gccctggccg    3480
gcagcagggg caggggtgg gaggcagcgg gggctgtggg gaatgaaggg gtttctcctg    3540
cagcccagga gacagagggg tgtgtctcac acagcagatt ggacacaggt gtttgcaagc    3600
agctgtcgtc acgtggctct ctggactggg ggcgtttgtc acggtcatct gtaggcctct    3660
gaatgtcagg gtgcgggttt ggttacaagg gattattagg ctggcagatg tcactcaccc    3720
acaagctgtc ctgacccagt cacacaaaga aagggaagag tggagtaatt aacagcccag    3780
cctcaagaca ggggccacct cccagctgtg tgacccagg caggccacct cttctctcca    3840
gcttcagttt ctttatctgt aaaatggggc caatttatag cacctgcttc ttagggctct    3900
tgtgaggatg aaatggacta atccatgcaa attttagcac agtgcctggc acagagtcag    3960
cctttgtgag tctgctgtta ctatatatcc tggtatggtc tgcagacaaa cttaaagaac    4020
ataaaagctt cacaatttga aaaggaacag cctacatgga taacctcttc cattgaaaaa    4080
ccatgaattt gttccttctg ttttcttctc cctactggct ctttttgtga aagttgtct    4140 taaaacttaa ctaaaattac aaggctcctt aagaactgcc tgaaaaaaat aattatggcc    4200
aagtgtggtg attcacacct gtaatcccag cactttggga ggcctagaca ggaggatcac    4260
tggagcccaa gagttcgaga ctagcctgag caacatagtg agacccgccc ccacctccc    4320 ctcaaccatc tctactaaaa ataaaaaaaa attaggaggg tgttgtggtg catgcctgca    4380
gtctcagata ctcaggagat ggaaggagga ggatggcttg agcccaggag ttggaggctg    4440
cagcgagccg tgatcatgcc actacactcc agcccaggca acatagcaag accctgtctc    4500
aaaaaaaaga aaaagaaaaa gtaataataa taattacaaa agttaaaaac caaagccagg    4560
catagtggta cacacctgtg gtcccagcta cttgggaggc tgaagcagga gaatgacttg    4620
agcctaggaa ttgaggctg cagtgagctg tgatcatgcc actgcactct agcctgggca    4680
acatagtgaa accctgtctc taaaaaaaaa tttttttatg ttaaaaaacc gtatgagctc    4740
ccactccctg ctggctccct ctaaagtggt ttaaaacaca gatgtaggag gcagatggtc    4800
tgggttcaaa tcctgctcca tagctggatg tggtggtgca ctcctgaggt actagctact    4860
tgggagactg aggcaggcgg aatgcttgag cccaggatt gaagatcagc ctgggcaaca    4920
tagcaagtcc ctgtctcaac aaacaaacaa acaaaaaaac aaaacaaaa tcccactcca    4980 ctactgagtt ctctgtgggg attataatta aaccagcctc actgggttgt gagaattcag    5040
tgagttcgct gagaagaggc ctagaacagg gcctggcaca cagtaggttc cagggcatcc    5100
```

-continued

```
ttgactgttg ctgttgttgg catcatcgtg cctcacccga taccttccag gaccccctgc   5160
ctgagcctcg cccccaccat actgggagat gcctggaggc cctgccttga tgctgaattt   5220
tgagaaagtc cctggagggg caggaggggt caggaggact tggaggggga tcacagggca   5280
actaattatt aaagcagata aagatgttta aaacagataa ggaagtcttt taatatttta   5340
atctgtaaag tctttaatct atgcaggcta atgtaaagtc tgtttactcc taatcatgtc   5400
tcaaaataac tccaccgggc attaccttgt ggggttggag agctggctgg tccagcccct   5460
cagaagctct cccctccccg cagggtgagg aggtcctccg gcagctgcag accctggcac   5520
caaagggcgt gaacgtccgc atcgctgtga gcaagcccag cgggcccag ccacaggcgg    5580 acctgcaggc tctgctgcag agcggtgagc tggggcccaa ctggggctgg tctgggcctg   5640
ggggtaccca gcctggcccc tgatctctgc ccctgctggt cacaggtgcc caggtccgca   5700
tggtggacat gcagaagctg acccatggcg tcctgcatac caagttctgg gtggtggacc   5760
agacccactt ctacctgggc agtgccaaca tggactggcg ttcactgacc caggtctgtc   5820
tgcaccctgt ctaccttcct tccaggccac tccctgcccc acagggcacc cagcctccga   5880
ctgcatccct cactcaatcc agagtcctct ccacccattc tctgtaatgg cttccttctt   5940
gcctcctacc aggcctccct aatccaagcc atgcacggtg gctcacacct ataatctcaa   6000
cactttggga ggccaaggtg ggaggattgc ttgagcccag gagttggaga ccagcctggg   6060
caacatagtg agacccatc tctaccaaaa aaaaaaaaat aagcccggtg tggtggcaca    6120
cacctctggt cccagctcct tgggagactg aggtgggagg atcacttgag cccaggagtt   6180
tgaggctaca gtgggttgta ttcatgccac tgcactccag cctgagtgac agagtgagac   6240
cctgttacaa aacaaagaat ccctaaatgg agccctctac tgccctcccc ctgctcctgg   6300
aagcctgggg ctccctctga tccccaattg cagctaccag cccctctaca tggcattcaa   6360
gaacctgcgc acccatttga tcttcattgt acatctctgt gtgcctgctc taagtccagc   6420
cctatcctgg gtaatgttgg gaacatggtg gtaacagatg gacctcatgg aactcccagc   6480
ccaatgcaga ctggcctgtc acctgacagt gacagcccag agggctcagg gccgggggttg  6540 gggagacaca ggcagagggt cagggccagg atggagggaa cagagggctg tggaagctca   6600
gagaccccaa cctggggcat tggagggttt cccaaaggag gtataactaa tctgatccct   6660
gaaggatagg gaggaattag cgcaagatgg aacaggaaac agcttgggca atgaggtgaa   6720
gataagacag gacaataact catgaattca tttcctcaac agatagttcc cctaacccttt  6780 aatctcagca attatgcagg gagatgctgt agatatagct gtgactgaga catccctagt   6840
gcctgtcctc ccagcccaat gggaagacca gtttgtcacc agaaagaatg aggagggaat   6900
cccaagggac tgtgagagcc cagaggaatg cctggtgcag gctgggtagt cacggagggc   6960
ttcctgaagg aggcaacatg tcagcctaga cctaagaatg agtagaagct agctcagtgg   7020
agggtagaag caacagcaga ttgcaaacgt tcaggaaacc tggagctttg gaataactga   7080 tttcatcaa aacttaagtt gataatcatt ctaggacttt agctattgga gctggggtgg    7140 aggggtact gtgggacagg gggaaagaca gagaccagc tggggagtgt ccctgtcatc     7200
tgtgagcact aggccgctat cgctgagctc agcactgccc tcctacaggt caaggagctg   7260
ggcgtggtca tgtacaactg cagctgcctg gctcgagacc tgaccaagat ctttgaggcc   7320
tactggttcc tgggccaggc aggcagctcc atcccatcaa cttggccccg gttctatgac   7380
acccgctaca accaagagac accaatggag atctgcctca atggaacccc tgctctggcc   7440
tacctggcgg tgagtctggg gcaagtgggg cctgtcatgt cccagcccca tgccgtcact   7500
```

```
cacagcctcc atctgtccct gtttggtgat gacagggagg gcgtatcctg accatcagtt      7560
ctcaccccag ctcattctgc ttggtcaggg gcctggagta gttcccaaca tccctcggcc      7620
tctatttcag ttagaaaatg gtattgttt ccaacctgtt agggctgctg ggagaggtac       7680
cctgggttca tgcacaccaa acctttggtg ctctatatca tccagtatag ccacaggtgg      7740
ctctttcagt ttaagttaat taaatgcaat taacaattca ggccaagtgg ggtggcttat      7800
gcctgtaatc ccaatacttt gggaggttga ggtgacagga tcacttgagg ccaggagttt      7860
gagaccagcc tggacaacat agcaagactc catctttaca aacaaacaaa caaacaaaca      7920
aaactagctg ggttgggttg tgcatgcatg tagtcacagc tacgcaggag gctgaggcag      7980
ggggatcact tgagcccagg aaatctaggc tgcagtgagc catgatcaca ccactgtact      8040
ccagcctggg tgacagcctg tttcaaaaaa aaattgtttc aagccaggca tggtttctca      8100
tccctgtaat cccagcactt tgggaggcca aggccaagat gggaggatca cttgaggcca      8160
ggagttcatg accagcctgg gcaacatagg gagacatcat ttctttctat ttttttttt      8220 ttttggtctt attatttatt gttctagata ggatacccaa gaactaggga gacaccattt      8280
ctacaaaaac ataatattaa ttaaaattag ccgggtgtgg ttgtgtgcac ctgtagtccc      8340
tggggaggct aagacagggg gatcacttga gcccaggagt ttgaggctgc gtgagctgat      8400
tgtaccactg cactccagcc tgggcaagag gctgttgccc tgtctccaaa aaagaaaaa      8460 attcagttcc tcatgcagta gccacatttc atatgctcag tagcacctgt agcaagtgac      8520
caccatattg gacatttcca tcactgtgac aggctctgtt ggacaacact ggctctcgcc      8580
atggcagata ctgatcactc tggacaaggc actgatgttt ctagctcttg atagtttcac      8640
tagttgaggc aggcaaccca ggtctcccta ggtcccctg agcaagttac ctgtccaagc       8700
ccagagtcat cgtggaaggc acaaccctaa ggcgtggacg tagggaagtg tgactcattg      8760
gggtctttca ctacaagggc ctcccgcagg ggatcaaggc tctcctcatt accacttccc      8820
cttttagagc ctcagtttcc ttgtctcttg agcattaagg aagatggggg gccaggcaca      8880
gtggctcatg cctgtaatcc tagcattttg ggagtccagg atgggcggat cacttgagct      8940
caggggttgg agaccagcct gggaaacgtg atgaaacccc atctctacca aaaatacaaa      9000
aattagcctg gagggtggc gggcacctgt aatcccagct actcgggagg ctgaggcagg       9060
agaatcactt gaacccagga ggtagaggtt gcagggagcc gagattgcac cattgccctc      9120
caggctgggt gacagagtga gactccactt caaaaaaaaa aaaggggggg gaagcggggg      9180
agcgggggaa ctgggaagag ggcctggtga ggcactgggc acccgagggg ttcccagtca      9240
aggcaggctg tgagcaaatc agggaagaaa gtgactcgag gctgggcaca gtggctcacg      9300
cctgtaatcc cagcactttg ggaggcctag gcaggtggat tgcctgaggt caggagttcg      9360
agacctgcct ggccaacatg gtgaaatccc atctccacta aaatacaaa aaattagct       9420 ggctatggtg atgtacgcct gtagtcccag ctacttggga ggctgaggca ggagaatcgc      9480
ttgaacccaa gaggcagcag aggttgcaat gagctgagat catgccactg cactccagcc      9540
taggagacag agcaagactc catctcaaaa aaaaaaaaa aaaaaagac ttgagcagag        9600 gtcctcaaac tgagcatgcc ccagaatcag ctgggcgggc ttgttaaaac ccagattcct      9660
ggaccccacc ccagcactct gattcagtag gccatgtgca gtgaggccca ggaatttgca      9720
tttctaacaa gttcccaggt gatgctgttg ccgctggatc agggacctta cgttgagaag      9780
cactgggtta gagcgtaaat tctggaacca gacagcctgg gttcgaatcc tggctccatt      9840
```

```
tatctgctgt gtgactttaa gtaagtcact taccctctct gagcctcagt ttcctcacat    9900
gtgaaatgga tgtggtgatt gaccctcttc ttcatggagg ctgaggattt ggtgagatcc    9960
acagtacctg gcttgtggtg agctgtccgt atgtggggtc cgttgtgacg atgaccctgg   10020
caggcacat gtcttaactg tcccctcgcc ctcagagtgc gcccccaccc ctgtgtccaa    10080
gtggccgcac tccagacctg aaggctctac tcaacgtggt ggacaatgcc cggagtttca   10140
tctacgtcgc tgtcatgaac tacctgccca ctctggagtt ctcccaccct cacaggtact   10200
gctgggtgtg gagataggga gccgctgcag ttggccagga gacgggagag ggaatcatgg   10260
agaccagaaa gctggtgggg gctccaggca aggggacaga tggaagagaa gctgcaggga   10320
gagacagtca ccaggaggtg accggaagaa ggtatctagg cacttgagac aggagaaaga   10380
gagattacag aggagacagg gatgaggttt caggacaagg tttgagggaa cagagaaaag   10440
gatgagaggg ccgggcgtgg tggctcacgc ctgtaatccc aacattttgc ggggctgagg   10500
tgggtggatc acttgaggtc aggagttcaa gaccagcctg gctaacatgg tgaaatccca   10560
tctctcctaa aaatacaaaa attagccggg cgtggtggca cgtgcttgta atcccagcta   10620
cttgagaggc tgaggcagga gaattgcttg aacctgggag gtgaaggttg cagtgagttg   10680
agatcgcgcc actgctctcc agcctgtgcg acagacagag caagactctg tctcaaaaaa   10740
acaacaaaaa aaaagagaag gctcagaata ttgggggttga gggcaggaag cctgaggcag   10800
gggtgcagga tgtgggattt ggggaggtag gaggcatggg ctggaaacag gatgaggggc   10860
ttggggggatg gggactaaaa gtatttgggt ttagggtagc aagcttgggg atttgtgatc   10920
ctgggataag aaggataaca accggccgga cgtggtggct cacacctgta atcccagcac   10980
tttgggaggc tgaggcgggt ggatcacgag gtcaggagat cgagaccatc ctggccaaca   11040
tggtgaagcc ccgtctctac taaaaataca aaaattagc caggtgtggt ggcaggcgcc   11100
tgtagtccca gctacttggg aggctgaggc aggagaatcg cttgaacccg ggagtcggag   11160
gttgcagtga gccaagatca tgccactgca ctccagcctg ggcgacggag cgagacacct   11220
tctcaaaaaa aaaaaaaga aaagaaaaaa aaaagaagg ataacaacca tacccactgc   11280
aacatccagg tggatgatgg cacttgtggg gctcaaagaa ggtattctag gggcagtaga   11340
taagacagtg ggtccaggca tggtggctca cgcctgtaat cccaacactt tgggaggccg   11400
aggcggaagg atccctagga gtttgagacc agcctgggca acataatgag accccgtctc   11460
tatagaaaaa ttggaagatt agcccagtgc ggtggcactc acctgcagtc ccagctactc   11520
aggagactga ggcaggagga tcacttgagc ccaggagttg gaggctgcat tgagctatgg   11580
tcgtgccact acactccagc ctgggtgata gagcaagaac ctgtctcaaa agaaaaaaaa   11640
agaggatgga ccgggcacag tggctcacgc ctgtaatccc agcactttgg gaggccaagg   11700
cgggcagatc acctgaggtc gggagttcga gaccagcctg acaaacatgg agaaaccccg   11760
tctctactaa aaatacaaaa ttagccaggc gtggtagcgc atgcctgtaa tcctagctac   11820
ccggagggct gaggcaggag aatcgcttga acccaggagg cagaggttgc agtgagccga   11880
gattgtgcca ttgcactcca gcgtgggcaa caagagcgaa attccacctc aaaaaaaaaa   11940
agaaagaaag aataaaagag gatgacaaca ctgggttttg gggagcagga atgggagcca   12000
cagccaggaa gaggaaatag ggatgtggga tttatggaga caggaacagg gtctgggagc   12060
cagcgatgag gaagtcctct caatagctaa agcagggccc aggcttggtt ccccaaagct   12120
gagggcaaag cctgtggaca cagccgccct ctgcatcctg ccccacctcc tatacacccg   12180
tcctcaggtt ctggcctgcc attgacgatg ggctgcggcg ggccacctac gagcgtggcg   12240
```

-continued

```
tcaaggtgcg cctgctcatc agctgctggg gacactcgga gccatccatg cgggccttcc   12300
tgctctctct ggctgccctg cgtgacaacc atacccactc tgacatccag gtggtaagta   12360
ctgccccaag ccaccccttg gccctgtgt ggggcagtcc tagggacaca gccctcatgg    12420
gactcgtctg tcaatgacaa gggcagccca gagtgagccc tgtcactgtg gggaaaccat   12480
gggtcagggc cagggtcatg gggcacaggg agaggggcca ggaccgggat gaggggcac    12540
aggcagaggg gttgggaccg ggatgggggt gcagagagag gtgttgggac caggaatggg   12600
gacatgggca ggtagagggg tcagggctgg gattgggagc acaggcagag gggtcagggc   12660
tgggatgggg aggcacaggc agaagggtcg gggccgggtt ggagggcaca gggagagggg   12720
ttagggccag ggttggggc acaggcagag gggtcgggc caggatggag gaggcccagg     12780
cagaggggtg agggcttggg gtgggggca cagagagagg gtttgggacc aggactgggg    12840
gagtgggcag gtagagggt cgggctggg gttgggggca caggcagagg ggtcagggct     12900
gggatggagg aggtacaggc agaggggtca gggctgggat ggggggcac aggcagaggg    12960
gtcagggctg ggatggagga ggcccaggca gaggggtcag ggcccagggt cgggggcac    13020
aggcagaggg gtcagggctg gggtggggat gcccagagga agcctctgcc ctagcgggaa   13080
gggccaagga agatgttctg gaaatggggg catctgagat gagacctcag gaatgaacag   13140
gagccattct gccgggaaca gtgttttgca aatgagacca ccggggcctc cctttcagct   13200
ttcgttctca gagggcccct ccacctggcc ctgttctggc cccgaggat tctgtgggaa    13260
gcagtggagt cccacagatc tcgctccaca ctctgctccc tgatcccggg gctcctccga   13320
ctccccctgc ctctcacact ccttcccatc ctccctccc actcagaaac tctttgtggt    13380
ccccgcggat gaggcccagg ctcgaatccc atatgcccgt gtcaaccaca acaagtacat   13440
ggtgactgaa cgcgccacct acatcggtga gtgtcttgag caccacgggg cgctgaagaa   13500
gagggggttc agacaccagg ggcggccccc cgagggtgcc cttatgctcc acccattcct   13560
ctctaggaac ctccaactgg tctggcaact acttcacgga gacggcgggc acctcgctgc   13620
tgtgacgca gaatggggag ggcggcctgc ggagccagct ggaggccatt ttcctgaggg    13680
actggactcc cccttacagc catgaccttg acacctcagc tgacagcgtg ggcaacgcct   13740
gccgcctgct ctgaggcccg atccagtggg caggccaagg cctgctgggc cccgcggac    13800
ccaggtgctc tgggtcacgg tccctgtccc cgcgccccg cttctgtctg cccccattgtg   13860
gctcctcagg ctctctcccc tgctctccca cctctacctc caccccacc ggcctgacgc    13920
tgtggccccg ggacccagca gagctggggg agggatcagc ccccaaagaa atgggggtgc   13980
atgctgggcc tggccccctg gcccacccc cactttccagg gcaaaaggg cccagggtta   14040
taataagtaa ataacttgtc tgtacagcct gtgcctgact gagtggtgtg agatggggtg   14100
caggggtagg ggacagctgg catgggcctc tggtggggac atctttttgt gctgagccct   14160
caacatgtca ctggcatgtg ctgagccctc agtgtgtgac cagtgtgggt tagcatgtac   14220
tgagccctca gcatgtgctg gcatggggttg gcatgtgctg agcccttaac atgtagtgta   14280
catgggctga cctgtgctga gcatgcagcg tgccaccctg tgcccggca tggacttagc    14340
actcatgtag ccagcatggg tatgtgctgc agagaagcat gttcccagat tgatcagcag   14400
ggaccaaacc attgccacat cccaagggtg aacaagcatg gctgagcacc agagtgtgca   14460
ccaagtgtga atttaggcct gccaagtgga tttacaccca gcacgtccca aatgtgggtg   14520
agtgcatgcc aaccctgtaa acatgtagga aggacaggtc aacagacaag gagaccccag   14580
```

-continued

```
catccggcaa acttgattaa cacatactga acacagcatg ttctgagggt ggattcccaa    14640
cacgccaagc acatagcgta tttaggacaa gggttagtca accaagcaca gcttttccct    14700
cctagtgtga cagcagccca ggctcccgcc taagccagtg gtcagctggg cccagcatcg    14760
cagagcaagt cactgggtgc cagcctggag cccccattcc ccccagggcc agtccaagcc    14820
ccaggcagtg agagcaggct tgaagcagga ctgctgaaca gttctatatt gaaatagaca    14880
gaggcagcag ggccaagggc gagcgcaggg ccagcggggt gcagccccct ttcctgctgt    14940
ccttctggcc aaggagcatg ggccagactc caaagccctg ctgtgtttag gagaggtgtg    15000
caggcacgca ccgcaccgca gacggggaat gagaatttct ggataactat ctttctgtaa    15060
gaataatttg tgggttcagg agatggctct gaggagcagt tcaggttggg agggaatgcc    15120
agcccagcta gcgcagcccc cagtgatggg caggggtgga atcaccatca gtggtgcccg    15180
gtgacatgct ggaggaagct ggtggccccc cggggtggac catgctggtg ggagcggcgg    15240
ggtgggagcc cctgagcccg tgggcccctg acgctctcca gggtgcagtc tggctcactc    15300
agccattctc caggacagct gctgggtcg aagagctcag ggtctggcct ctgtggggga    15360
agagagaggg gcatcagcca agcagtgtta gtgtattagt gtctgctgag cctctgtcac    15420
ctcctcctga tgagggtgag catgtgctag ggtcttacca gtgctgggcc tttattgccc    15480
ctttgtagtg atgtgatgac agctcactgc agcctcgacc tccctggctc aagtgatcct    15540
cccacctcag cctcctgagt agctgggact acaggtgcat gccaccaaaa ccagctaata    15600
tttctaattt tttggtgcag acgggatctc actatgttgc ccaggctctt tatcaagctt    15660
cttataagta gattactgtg ccctgagttt ttgtcacagc ctggaagtag ctgagtaagt    15720
gctgagcctt atcatatctt gacggtatta ggtgtgtgct gagcctccta agtccctaat    15780
tgtatcctga acatgggtga gtgtgtgttg agcctcctca cacactaatc atatcctgag    15840
cacgggtgag tgtgtgctga gcctcctccc accctaatcg tatcctgaac gcacccggct    15900
cacctcagct tccatggtca tgttgtcaat gttgggccca tcctcatctc gctgcaggat    15960
ggccagtggc tcagcagagg ccccgagatg ctctccttcc tcccagctgc tgccccggca    16020
gggcctgtca tcctcaggcg agacctggct cagccgaatg agg                      16063
```

<210> SEQ ID NO 4
<211> LENGTH: 437
<212> TYPE: PRT
<213> ORGANISM: Homo sapiens

<400> SEQUENCE: 4

```
Met Thr Gln Leu Phe Leu Trp Glu Tyr Gly Asp Leu His Leu Phe Gly
 1               5                  10                  15

Pro Asn Gln Arg Pro Ala Pro Cys Tyr Asp Pro Cys Glu Ala Val Leu
            20                  25                  30

Val Glu Ser Ile Pro Glu Gly Leu Asp Phe Pro Asn Ala Ser Thr Gly
        35                  40                  45

Asn Pro Ser Thr Ser Gln Ala Trp Leu Gly Leu Ala Gly Ala His
    50                  55                  60

Ser Ser Leu Asp Ile Ala Ser Phe Tyr Trp Thr Leu Thr Asn Asn Asp
65                  70                  75                  80

Thr His Thr Gln Glu Pro Ser Ala Gln Gln Gly Glu Glu Val Leu Arg
                85                  90                  95

Gln Leu Gln Thr Leu Ala Pro Lys Gly Val Asn Val Arg Ile Ala Val
           100                 105                 110
```

```
Ser Lys Pro Ser Gly Pro Gln Pro Gln Ala Asp Leu Gln Ala Leu Leu
        115                 120                 125

Gln Ser Gly Ala Gln Val Arg Met Val Asp Met Gln Lys Leu Thr His
130                 135                 140

Gly Val Leu His Thr Lys Phe Trp Val Val Asp Gln Thr His Phe Tyr
145                 150                 155                 160

Leu Gly Ser Ala Asn Met Asp Trp Arg Ser Leu Thr Gln Val Lys Glu
                165                 170                 175

Leu Gly Val Val Met Tyr Asn Cys Ser Cys Leu Ala Arg Asp Leu Thr
                180                 185                 190

Lys Ile Phe Glu Ala Tyr Trp Phe Leu Gly Gln Ala Gly Ser Ser Ile
        195                 200                 205

Pro Ser Thr Trp Pro Arg Phe Tyr Asp Thr Arg Tyr Asn Gln Glu Thr
210                 215                 220

Pro Met Glu Ile Cys Leu Asn Gly Thr Pro Ala Leu Ala Tyr Leu Ala
225                 230                 235                 240

Ser Ala Pro Pro Leu Cys Pro Ser Gly Arg Thr Pro Asp Leu Lys
                245                 250                 255

Ala Leu Leu Asn Val Val Asp Asn Ala Arg Ser Phe Ile Tyr Val Ala
                260                 265                 270

Val Met Asn Tyr Leu Pro Thr Leu Glu Phe Ser His Pro His Arg Phe
        275                 280                 285

Trp Pro Ala Ile Asp Asp Gly Leu Arg Arg Ala Thr Tyr Glu Arg Gly
290                 295                 300

Val Lys Val Arg Leu Leu Ile Ser Cys Trp Gly His Ser Glu Pro Ser
305                 310                 315                 320

Met Arg Ala Phe Leu Leu Ser Leu Ala Ala Leu Arg Asp Asn His Thr
                325                 330                 335

His Ser Asp Ile Gln Val Lys Leu Phe Val Val Pro Ala Asp Glu Ala
                340                 345                 350

Gln Ala Arg Ile Pro Tyr Ala Arg Val Asn His Asn Lys Tyr Met Val
        355                 360                 365

Thr Glu Arg Ala Thr Tyr Ile Gly Thr Ser Asn Trp Ser Gly Asn Tyr
370                 375                 380

Phe Thr Glu Thr Ala Gly Thr Ser Leu Leu Val Thr Gln Asn Gly Arg
385                 390                 395                 400

Gly Gly Leu Arg Ser Gln Leu Glu Ala Ile Phe Leu Arg Asp Trp Asp
                405                 410                 415

Ser Pro Tyr Ile His Asp Leu Asp Thr Ser Ala Asp Ser Val Gly Asn
                420                 425                 430

Ala Cys Arg Leu Leu
        435

<210> SEQ ID NO 5
<211> LENGTH: 488
<212> TYPE: PRT
<213> ORGANISM: Mus musculus

<400> SEQUENCE: 5

Met Lys Pro Lys Leu Met Tyr Gln Glu Leu Lys Val Pro Val Glu Glu
1               5                   10                  15

Pro Ala Gly Glu Leu Pro Leu Asn Glu Ile Glu Ala Trp Lys Ala Ala
                20                  25                  30

Glu Lys Lys Ala Arg Trp Val Leu Leu Val Leu Ile Leu Ala Val Val
            35                  40                  45
```

```
Gly Phe Gly Ala Leu Met Thr Gln Leu Phe Leu Trp Glu Tyr Gly Asp
    50                  55                  60

Leu His Leu Phe Gly Pro Asn Gln Arg Pro Ala Pro Cys Tyr Asp Pro
65                  70                  75                  80

Cys Glu Ala Val Leu Val Glu Ser Ile Pro Glu Gly Leu Glu Phe Pro
                85                  90                  95

Asn Ala Thr Thr Ser Asn Pro Ser Thr Ser Gln Ala Trp Leu Gly Leu
            100                 105                 110

Leu Ala Gly Ala His Ser Ser Leu Asp Ile Ala Ser Phe Tyr Trp Thr
            115                 120                 125

Leu Thr Asn Asn Asp Thr His Thr Gln Glu Pro Ser Ala Gln Gln Gly
        130                 135                 140

Glu Glu Val Leu Gln Gln Leu Gln Ala Leu Ala Pro Arg Gly Val Lys
145                 150                 155                 160

Val Arg Ile Ala Val Ser Lys Pro Asn Gly Pro Leu Ala Asp Leu Gln
                165                 170                 175

Ser Leu Leu Gln Ser Gly Ala Gln Val Arg Met Val Asp Met Gln Lys
            180                 185                 190

Leu Thr His Gly Val Leu His Thr Lys Phe Trp Val Asp Gln Thr
        195                 200                 205

His Phe Tyr Leu Gly Ser Ala Asn Met Asp Trp Arg Ser Leu Thr Gln
        210                 215                 220

Val Lys Glu Leu Gly Val Val Met Tyr Asn Cys Ser Cys Leu Ala Arg
225                 230                 235                 240

Asp Leu Thr Lys Ile Phe Glu Ala Tyr Trp Phe Leu Gly Gln Ala Gly
                245                 250                 255

Ser Ser Ile Pro Ser Thr Trp Pro Arg Ser Phe Asp Thr Arg Tyr Asn
            260                 265                 270

Gln Glu Thr Pro Met Glu Ile Cys Leu Asn Gly Thr Pro Ala Leu Ala
        275                 280                 285

Tyr Leu Ala Ser Ala Pro Pro Pro Leu Cys Pro Ser Gly Arg Thr Pro
    290                 295                 300

Asp Leu Lys Ala Leu Leu Asn Val Val Asp Ser Ala Arg Ser Phe Ile
305                 310                 315                 320

Tyr Ile Ala Val Met Asn Tyr Leu Pro Thr Met Glu Phe Ser His Pro
                325                 330                 335

Arg Arg Phe Trp Pro Ala Ile Asp Asp Gly Leu Arg Arg Ala Ala Tyr
            340                 345                 350

Glu Arg Gly Val Lys Val Arg Leu Leu Ile Ser Cys Trp Gly His Ser
        355                 360                 365

Asp Pro Ser Met Arg Ser Phe Leu Leu Ser Leu Ala Ala Leu His Asp
    370                 375                 380

Asn His Thr His Ser Asp Ile Gln Val Lys Leu Phe Val Val Pro Thr
385                 390                 395                 400

Asp Glu Ser Gln Ala Arg Ile Pro Tyr Ala Arg Val Asn His Asn Lys
                405                 410                 415

Tyr Met Val Thr Glu Arg Ala Ser Tyr Ile Gly Thr Ser Asn Trp Ser
            420                 425                 430

Gly Ser Tyr Phe Thr Glu Thr Ala Gly Thr Ser Leu Leu Val Thr Gln
        435                 440                 445

Asn Gly His Gly Gly Leu Arg Ser Gln Leu Glu Ala Val Phe Leu Arg
    450                 455                 460
```

```
-continued

Asp Trp Glu Ser Pro Tyr Ser His Asp Leu Asp Thr Ser Ala Asn Ser
465                 470             475              480

Val Gly Asn Ala Cys Arg Leu Leu
                485
```